US009062287B2

(12) United States Patent
Ideno et al.

(10) Patent No.: US 9,062,287 B2
(45) Date of Patent: Jun. 23, 2015

(54) PROCESS FOR PRODUCTION OF NATURAL KILLER CELLS

(75) Inventors: Mitsuko Ideno, Otsu (JP); Mie Yabuuchi, Otsu (JP); Meiko Jin, Otsu (JP); Masae Sato, Otsu (JP); Naoko Ashida, Otsu (JP); Tatsuji Enoki, Otsu (JP)

(73) Assignee: TAKARA BIO INC., Shiga (JP)

( * ) Notice: Subject to any disclaimer, the term of this patent is extended or adjusted under 35 U.S.C. 154(b) by 79 days.

(21) Appl. No.: 13/394,398

(22) PCT Filed: Sep. 10, 2010

(86) PCT No.: PCT/JP2010/065615
§ 371 (c)(1),
(2), (4) Date: Mar. 6, 2012

(87) PCT Pub. No.: WO2011/030851
PCT Pub. Date: Mar. 17, 2011

(65) Prior Publication Data
US 2012/0171173 A1  Jul. 5, 2012

(30) Foreign Application Priority Data
Sep. 11, 2009 (JP) ................. 2009-210178

(51) Int. Cl.
C12N 5/0783 (2010.01)
A61K 35/12 (2006.01)

(52) U.S. Cl.
CPC ...... *C12N 5/0646* (2013.01); *C12N 2502/1114* (2013.01); *A61K 2035/124* (2013.01); *C12N 2500/72* (2013.01); *C12N 2501/2302* (2013.01); *C12N 2501/24* (2013.01); *C12N 2501/515* (2013.01)

(58) Field of Classification Search
None
See application file for complete search history.

(56) References Cited

U.S. PATENT DOCUMENTS

| 6,426,042 | B1 | 7/2002 | Asada et al. |
| 2005/0227354 | A1 | 10/2005 | Sagawa et al. |
| 2007/0207187 | A1 | 9/2007 | Yajima et al. |
| 2009/0068141 | A1 | 3/2009 | Parkhurst et al. |
| 2010/0068192 | A1 | 3/2010 | Enoki et al. |
| 2010/0150886 | A1 | 6/2010 | Marui et al. |
| 2010/0255578 | A1 | 10/2010 | Muraki et al. |

FOREIGN PATENT DOCUMENTS

| CN | 101400785 A | 4/2009 |
| JP | 2006-160694 | 6/2006 |
| JP | 2008-127277 | 6/2008 |
| WO | 97/18318 | 5/1997 |
| WO | 00/09168 | 2/2000 |
| WO | 03/080817 | 10/2003 |
| WO | 2007/020880 | 2/2007 |
| WO | 2007/103901 | 9/2007 |
| WO | 2007/142300 | 12/2007 |

OTHER PUBLICATIONS

Chinese Office Action dated Nov. 1, 2012 issued in corresponding application No. 201080050641.8 with English translation.
K. Yamamoto et al., "Effects of OK-432 on the Proliferation and Cytotoxicity of Lymphokine-Activated Killer (LAK) Cells", Journal of Immunotherapy, vol. 22, No. 1, pp. 33-40, 1999.
H. Rabinowich et al., "Increased Proliferation, Lytic Activity, and Purity of Human Natural Killer Cells Cocultured with Mitogen-Activated Feeder Cells", Cellular Immunology, vol. 135, No. 2, pp. 454-470, 1991.
R. J. Morris et al., "A High-Efficiency System of Natural Killer Cell Cloning", Journal of Immunological Methods, vol. 307, No. 1-2, pp. 24-33, 2005.
M. Takahashi, "Biological Response Modifiers Inhibit Experimental Metastases and Induce Interleukin-12 Production", Tohoku University Dental Journal, vol. 15, No. 2, pp. 132-144, 1996 (with English abstract).
D. Cho et al., "Expansion and Activation of Natural Killer Cells for Cancer Immunotherapy", Korean J. Lab Med., vol. 29, pp. 89-96, 2009.
E. Ruoslahti et al., "Alignment of Biologically Active Domains in the Fibronectin Molecule", The Journal of Biological Chemistry, vol. 256, No. 14, pp. 7277-7281, Jul. 25, 1981.
F. Kimizuka et al., "Production and Characterization of Functional Domains of Human Fibronectin Expressed in *Escherichia coli*", J. Biochem., vol. 110, pp. 284-291, 1991.
A. R. Kornblihtt et al., "Primary Structure of Human Fibronectin: Differential Splicing may Generate at least 10 Polypeptides from a Single Gene", The EMBO Journal, vol. 4, No. 7, pp. 1755-1759, 1985.
K. Sekiguchi et al., "Human Liver Fibronectin Complementary DNAs: Identification of Two Different Messenger RNAs Possibly Encoding the α and β Subunits of Plasma Fibronectin", Biochemistry, vol. 25, pp. 4936-4941, 1986.
P. C. Kung et al.,"Monoclonal Antibodies Defining Distinctive Human T Cell Surface Antigens", Science, vol. 206, pp. 347-349, Oct. 19, 1979.
U. Koehl et al., "Ex vivo Expansion of Highly Purified NK Cells for Immunotherapy after Haploidentical Stem Cell Transplantation in Children", Klin Padiatr, vol. 217, pp. 345-350, 2005.
E. A. Grimm et al., "Lymphokine-Activated Killer Cell Phenomenon", Journal of Experimental Medicine, vol. 155, pp. 1823-1841, Jun. 1982.

(Continued)

*Primary Examiner* — Allison Fox
(74) *Attorney, Agent, or Firm* — Wenderoth, Lind & Ponack, L.L.P.

(57) ABSTRACT

A process for producing a cell mass containing natural killer cells, characterized by involving a step of carrying out the expansion culture of a cell mass containing natural killer cells and/or cells capable of being differentiated into natural killer cells in the presence of a biological response modifier and cells that has been so treated as to lose a proliferation capability, and others.

7 Claims, No Drawings

(56) References Cited

OTHER PUBLICATIONS

English translation of International Preliminary Report on Patentability and Written Opinion dated May 30, 2012.
Supplementary European Search Report dated Mar. 5, 2013 in EP Application No. 10815445.1.
J. Luhm et al., "Large-Scale Generation of Natural Killer Lymphocytes for Clinical Application", Journal of Hematotherapy & Stem Cell Research, vol. 11, No. 4, pp. 651-657, Jan. 1, 2002.
T. Sudo et al., "OK432-Actived Natural Killer Cells Enhanced Trastuzumab (Herceptin®)-Mediated Antibody-Dependent Cellular Cytotoxicity in Patients with Advanced Cancer", Anticancer Research, vol. 26, pp. 4327-4334, Nov. 1, 2006.
Chinese Office Action issued Jul. 23, 2013 in corresponding Chinese Application No. 201080050641.8 (with English translation).
Decision on Rejection dated Aug. 28, 2014 issued in the corresponding Chinese Patent Application No. 201080050641.8, with English translation thereof.
Chinese Office Action issued Feb. 8, 2014 in corresponding Chinese Application No. 201080050641.8 (with English translation).
Office Action issued Dec. 16, 2014 in corresponding Japanese Patent Application No. 2011-530886 (with English translation).
Kobayashi et al. "Preparation of NK-Enriched LAK Cells—Their Potential Cytotoxic and ADCC Activities", Jpn. J. Cancer Chemother., vol. 30(11), pp. 1776-1779, Oct. 2003 (with English abstract).

PROCESS FOR PRODUCTION OF NATURAL KILLER CELLS

This application is a U.S. national stage of International Application No. PCT/JP2010/065615 filed Sep. 10, 2010.

TECHNICAL FIELD

The present invention relates to a method of obtaining a high purity natural killer cell population useful in the medical field.

The present application claims the priority based on Japanese Patent Application No. 2009-210178 filed on Sep. 11, 2009, the entire content of which is incorporated herein.

BACKGROUND ART

A natural killer cell (NK cell) is a lymphoid cell playing a role in an immune reaction. Since the natural killer cell has a variety of functions and particularly has strong activity of killing a tumor cell, it is believed that the cell is an important member of immunological surveillance mechanism for removing abnormal cells which have become tumorigenic or are becoming tumorigenic in a living body. Therefore, study for effectively utilizing the cell in tumor therapy has been conducted for a long time.

For example, when a large amount of interleukin (IL)-2 which is one kind of lymphokines is added to a culture medium of a peripheral blood mononuclear cell (PBMC), so-called lymphokine activated killer lymphocytes (LAK cells) are proliferated in around one week in the case of a human. The LAK cells are well-known to comprise many NK cells. The LAK cells are widely used in adoptive immunotherapy of tumors. The LAK cells are also known to be effective in infectious diseases, and draw attention as strategy for treating infectious diseases which are difficult to cure with antibiotics.

Until now, a number of methods of ex vivo culturing NK cells have been reported (e.g. Non-Patent Literature 1), which are classified into a method with an accessory cell and a method without an accessory cell. The method without an accessory cell is a method comprising stimulating PBMC with IL-2 or IL-15. However, this method often results in a low cell expansion rate and a low NK cell content rate after culturing, and therefore, NK cells may not be obtained in an amount necessary for treatment depending on a donor of PBMC. Further, it has been reported that when a culture period is prolonged in order to obtain a large amount of NK cells, cytotoxic activity is reduced.

On the other hand, the method with an accessory cell is, for example, a method comprising using a K562 cell which is a B lymphoma cell strain, a Daudi cell which is a malignant lymphoma cell strain, or a HFWT cell which is a Wilms tumor cell strain, which has been subjected to radiation. Further, a method comprising using as an accessory cell the above-mentioned tumor cells into which a cytokine expressing gene is transferred has been also reported. However, since these accessory cells are tumor cells, allo cells and gene-transferred cells, much attention is necessary for securing safety from a viewpoint of injection into a living body of a NK cell mixed cultured with an accessory cell. In addition, a method comprising using PBMC irradiated with radiation as an accessory cell has been also reported (Patent Literature 1). However, this method necessitates a step of removing a CD3-positive cell as a cell population containing a NK cell, and further necessitates preparing a large amount of PBMC from a donor.

A cell expansion rate by this method is maximally about 140-fold after 22 days from the initiation of culture.

A bioresponse modifying agent is a substance which regulates immune mechanism of a living body and is expected to have therapeutic effect on a variety of diseases, and is used in immunotherapy of a cancer. However, it is known that the agent does not activate lymphocyte function to such an extent that is expected. For this reason, such a treatment that the agent is directly administered to a patient requiring activation of lymphocyte function to activate the function is not generally performed, and is used only on limited cases under the current circumstances. The action mechanism of the bioresponse modifying agent does not comprise direct action on a tumor cell, and it is believed that the bioresponse modifying agent activates an immune cell inherent to a living body to which the agent is administered, and exerts anti-tumor effect via action of the immune cell. Therefore, the effect of administration of the bioresponse modifying agent is greatly influenced by the natural immunological state of a living body which has received the administration of the bioresponse modifying agent, and undergoes influence of a background factor of the living body. Thus, it is said that there are often differences of the anti-tumor effect between individuals and differences of action strength depending on the clinical states of patients.

CITATION LIST

Patent Literatures

Patent Literature 1: WO2007/103901

Non-Patent Literatures

Non-Patent Literature 1: Cho D and Campana D, Korean J Lab Med, 2009, vol. 29, p. 89-96

DISCLOSURE OF INVENTION

Problems to be Solved by the Invention

Regarding a NK cell which is expected to have high therapeutic effect, a method of effectively obtaining a high purity NK cell has not been established under the current circumstances. Therefore, development of a further cell proliferation method for preparing a NK cell has been demanded.

Solutions to the Problems

The present inventors intensively continued to study various conditions of culture, particularly expansion culture of a lymphocyte and, as a result, found out a method of efficiently expansion-culturing a NK cell. Thus, the present invention was completed.

That is, the present invention relates to:
[1] A process for preparing a cell population containing a natural killer cell, comprising a step of expansion-culturing a cell population containing a natural killer cell and/or a cell capable of differentiating into a natural killer cell, in the presence of a biorespoce modifying agent and a cell which has been subjected to a treatment of diminishing the proliferation ability,
[2] The process according to [1], wherein the bioresponse modifying agent is a bacterium-derived preparation,
[3] The process according to [2], wherein the bioresponse modifying agent is a preparation derived from a bacterium selected from the group consisting of OK-432, BCG, *Streptcoccus pyogenes, Corynebacterium parvum* and a cell wall skeleton thereof,

[4] The process according any one of [1] to [3], wherein the cell which has been subjected to a treatment of diminishing the proliferation ability is a cell selected from the group consisting of a peripheral blood mononuclear cell, a T cell, a T cell subset and a B cell which has been subjected to a treatment of diminishing the proliferation ability,

[5] The process according to [4], wherein the cell which has been subjected to a treatment of diminishing the proliferation ability is an artificially expansion-cultured T cell which has been subjected to a treatment of diminishing the proliferation ability,

[6] The process according to any one of [1] to [5], wherein the cell which has been subjected to a treatment of diminishing the proliferation ability is a cell derived from the same individual as that of the natural killer cell or the cell capable of differentiating into a natural killer cell,

[7] The process according to any one of [1] to [6], wherein the step of expansion-culture in the presence of a cell which has been subjected to a treatment of diminishing the proliferation ability comprises performing addition of the cell plural times,

[8] The process according to any one of [1] to [6], wherein a peripheral blood mononuclear cell is used as the natural killer cell and/or the cell capable of differentiating into a natural killer cell,

[9] A cell population obtained by the process according to any one of [1] to [8],

[10] A cell subpopulation containing a NK cell separated from the cell population according to [9],

[11] A medicament containing the cell population according to [9] and/or the cell subpopulation according to [10],

[12] Use of the cell population according to [9] and/or the cell subpopulation according to [10] for producing a medicament,

[13] A method of treating or preventing a disease, comprising a step of administering an effective amount of the cell population according to [9] and/or the cell subpopulation according to [10] to a subject,

[14] A process for preparing a cell population and/or a cell subpopulation containing a natural killer cell, comprising a step of freezing the cell population according to [9] and/or the cell subpopulation according to [10], thawing the frozen cell population and/or cell subpopulation, and then culturing the cell population and/or cell subpopulation in the presence of a cytokine, and

[15] A process for preparing a cell population containing a natural killer cell, comprising a step of expansion-culturing an isolated and/or purified cell population containing a natural killer cell and/or a cell capable of differentiating into a natural killer cell, in the presence of a bioresponse modifying agent.

Effects of the Invention

According to the present invention, a novel process for preparing a NK cell is provided. Since the process of the present invention can afford a cell having a high cell proliferation rate and strong cytotoxic activity, the NK cell obtained by the present invention can be preferably used, for example, in adoptive immunotherapy. Therefore, it is expected that the process of the present invention greatly contributes to the medical field.

MODE FOR CARRYING OUT THE INVENTION

As used herein, a "NK cell" means a cell population containing a large granular lymphocyte which non-MHC-crestrictedly injures a tumor cell and a virus-infected cell without antigen sensitization and works for maintaining homeostasis of a living body. As representative surface markers of the NK cell, CD56, CD94 and CD16 are known. In addition, the NK cell is negative for CD3.

As used herein, a "peripheral blood mononuclear cell (PBMC)" means a cell population containing a lymphocyte and a monocyte derived from peripheral blood, and includes a T cell, a B cell, and a NK cell.

As used herein, a "polypeptide having an amino acid sequence derived from fibronectin" means a polypeptide containing an amino acid sequence derived from fibronectin, or a part thereof in the molecule, and examples thereof include fibronectin or a fragment of fibronectin. Fibronectin or a fragment of fibronectin may be any of a naturally-derived isolated polypeptide, an artificially synthesized polypeptide, or a recombinant polypeptide prepared by genetic engineering. Fibronectin can be prepared in a substantially pure form from a naturally occurring substance, for example, based on the disclosure of Ruoslahti E. et al., J. Biol. Chem., vol. 256, No. 14, p. 7277-7281 (1981). Herein, fibronectin or a polypeptide having an amino acid sequence derived from fibronectin used in the present invention does not substantially contain other proteins which exist with fibronectin in nature. The above-mentioned polypeptides can be used alone or as a mixture of plural kinds in the present invention.

In addition, there are many known splicing variants of fibronectin. The polypeptide used in the present invention may be a polypeptide having an amino acid sequence derived from any variant, as long as it produces the desired effect of the present invention. For example, in the case of fibronectin derived from plasma, it is known that a region called ED-B present upstream of a cell binding domain, and a region called ED-A present between a cell binding domain and a heparin binding domain are deleted. A polypeptide having an amino acid sequence of such plasma-derived fibronectin can be also used in the present invention.

Useful information for a fibronectin fragment which can be used in the present invention, and preparation of the fragment can be obtained from J. Biochem., vol. 110, p. 284-291 (1991), EMBO J., vol. 4, No. 7, p. 1755-1759 (1985), Biochemistry, vol. 25, No. 17, p. 4936-4941 (1986), WO2007/142300 etc. In addition, a nucleic acid sequence encoding fibronectin and an amino acid sequence of fibronectin are disclosed in Genbank Accession No. NM 002026, and NP_002017.

The domain structure of fibronectin is divided into seven domains. The amino acid sequence of fibronectin contains three kinds of similar sequences, and the whole is comprised of repeats of each of these sequences. The three kinds of similar sequences are called type I, type II and type III, respectively. Among them, type III is comprised of 71 to 96 amino acid residues, and the matching rate of these amino acid residues is 17 to 40%. There are 14 type III sequences in fibronectin and, among them, the eighth, ninth and tenth sequences (hereinafter, referred to as III-8, III-9 and III-10, respectively) are contained in a cell-binding domain, and the twelfth, thirteenth and fourteenth sequences (hereinafter, referred to as III-12, III-13 and III-14, respectively) are contained in a heparin-binding domain. In addition, a region called IIICS exists at the C-terminal side of the heparin-binding domain. In IIICS, there is a region called CS-1 which consists of 25 amino acid residues and which has activity of binding with VLA-4. The fibronectin fragment which can be used in the present invention may be a fragment comprising any domain of III-7, 8, 9, 11, 12, 13 or CS-1 or, further, may be a fragment in which plural domains are repeatedly connected. Examples of the fibronectin fragment which can be used in the present invention include fragments containing a cell adhesion domain comprising a ligand to VLA-5, a heparin-binding domain, or a CS-1 domain which is a ligand to VLA-4. Examples of the fragment include CH-271, CH-296, H-271, and H-296 described in J. Biochem., vol. 110, pp. 284-291 (1991), and derivatives or modifications thereof. The CH-296 is commercially available under the name of RetroNectin (registered trademark).

Herein, the "bioresponse modifying agent" is also called Biological response modifier (BRM) and means a group of substances which improve nonspecific immunological responding ability in a living body. As the bioresponse modifying agent, bacteria-derived preparations [OK-432, BCG (Bacillus Calmette Guerin), *Streptcoccus pyogenes, Corynebacterium parvum* and cell wall skeletons thereof], basidiomycete-derived polysaccharides (lentinan, schizophyllan, PSK etc.), synthetic substances (pyran copolymer, levamisole etc.), and cytokines are known. "OK-432" means a general name of bacteria-derived preparations obtained by treating an attenuated natural mutant strain (Su strain) of A-group 3-type hemolytic Streptcoccus pyogenes with penicillin. This preparation is sold under Picibanil (registered trademark) as a trade name.

The present invention will be specifically explained below.

As used herein, a "treatment of diminishing the proliferation ability" is not particularly limited as long as the treatment makes a cell lose or reduce its proliferation ability. Examples of the treatment include a chemical treatment and/or a physical treatment. Examples of the chemical a treatment include treatment with a chemical drug (formalin etc.) and a treatment with an anti-cancer agent (mitosis inhibitor, for example, mitomycin C etc.). Examples of the physical treatment include a radiation treatment, a mild heat (heating/warming) treatment, a freezing/thawing treatment or an ultrasound treatment. For example, when the treatment is performed by radiation, for example, a γ-ray and an X-ray can be used.

Since a cell which has been subjected to a treatment of diminishing the proliferation ability loses or reduces the ability relating to proliferation such as cell division and DNA synthesis, the proliferation ability of the cell is reduced as compared with a cell which has not been treated. For example, although a cell which has been subjected to a radiation treatment reduces the proliferation ability, the cell exhibits the same form and character as those of a living cell immediately after the treatment and maintains the metabolizing ability to secrete a protein such as a cytokine etc.

1. Process for Preparing NK Cell

The process for preparing a NK cell of the present invention comprises a step of expansion-culturing a cell population containing a NK cell and/or a cell capable of differentiating into a NK cell in the presence of a bioresponse modifying agent and a cell which has been subjected to a treatment of diminishing the proliferation ability. According to the process for preparing a NK cell of the present invention, as compared with a conventional process, a cell population having an extremely higher expansion culturing rate, an extremely higher NK cell content rate, and an extremely higher cytotoxic activity of a NK cell can be stably prepared. Herein, the expansion culturing rate means a proliferation rate relative to the time of culture initiation, and the rate is calculated by dividing the cell number at the end of culture by the cell number at the initiation of culture, and then dividing the resulting value by a rate of the number of cells used when subcultured.

One characteristic of the process of the present invention is use of a cell which has been subjected to a treatment of diminishing the proliferation ability. The cell to be subjected to a treatment of diminishing the proliferation ability is not particularly limited. In a preferable aspect of the present invention, PBMC, a T cell, a T cell subset (e.g. CD4-positive T cell, CD8-positive T cell etc.), a B cell or a cell population prepared by culturing these cells is used.

A process for preparing PBMC is not particularly limited. PBMC can be prepared from blood or blood cell components obtained by separating plasma from blood, by a known method, for example, a density gradient centrifugation method. A B cell, a T cell or a T cell subset can be separated from PBMC or another biological sample (peripheral blood, bone marrow fluid, umbilical blood etc.) by a known method. Further, a cell population obtained by culturing the aforementioned cell to increase the cell number can be also used in the present invention. For example, a T cell population obtained by expansion culturing a cell population containing a T cell or a precursor cell of a T cell is also used. Proliferation efficiency of a T cell is improved by coexistence of the polypeptide having an amino acid sequence derived from fibronectin in the preparation of the T cell population. That is, a large amount of T cells can be obtained from a small amount of material (blood or PBMC).

The expansion culture of a T cell in the presence of the polypeptide having an amino acid sequence derived from fibronectin is performed as follows.

The cell population to be cultured in the presence of the polypeptide having an amino acid sequence derived from fibronectin may be a cell population containing a T cell or a precursor cell of a T cell, and a body fluid such as peripheral blood, bone marrow fluid, umbilical blood, and a lymph fluid can be used. Alternatively, a cell population separated from these body fluids, or each body part or organ, for example, PBMC, a T cell, a T cell subset or a mixture thereof can be used. In preparation of a NK cell to be transplanted into a living body for the purpose of treatment, these cells or cell populations can be derived from the same individual, that is, the same donor as that of "a NK cell and/or a cell capable of differenting into a NK cell" described later. Particularly preferably, it is desirable that both of the "NK cell and/or a cell capable of differentiating into a NK cell" and the "cell which has been subjected to a treatment of diminishing the proliferation ability" are derived from a patient itself.

The culture of a cell population in the presence of the polypeptide having an amino acid sequence derived from fibronectin can be performed with reference to the detail description of WO 03/080817. When a cell population is cultured in the presence of the polypeptide having an amino acid sequence derived from fibronectin, an expansion culturing rate becomes extremely high and a large amount of cells can be easily prepared.

The cell concentration at culture initiation for the T cell expansion culture is for example 1 to $1\times10^8$ cells/mL, preferably 10 to $5\times10^7$ cells/mL, and further preferably $1\times10^2$ to $2\times10^7$ cells/mL, but not particularly limited to them.

A medium used for the T cell expansion culture may be a known medium used for cell culture, and the medium may further contain various cytokines, suitable proteins or other components. Examples of the cytokines include IL-2, IL-7, IL-12, IL-15, IFN-γ etc. Preferably, a medium containing IL-2 is used. The concentration of IL-2 in the medium is not particularly limited, and the medium may contain preferably 0.01 to $1\times10^5$ U/mL, more preferably 1 to $1\times10^4$ U/mL of IL-2. Examples of the suitable proteins include an anti-CD3 antibody and an anti-IL-4 antibody. Examples of the anti-CD3 antibody used in the present invention include, but not limited to, preferably an anti-human CD3 monoclonal antibody, more preferably OKT3 [Science, 1979, vol. 206, p. 347-349]. A lymphocyte stimulating factor such as lectin etc. can be also added to the medium. Further, a medium comprising a bisphosphinic acid-based compound such as pamidronate or zoledronate, a pyrophosphoric acid monoester-based compound such as isopentenylpyrophosphoric acid or 2-methyl-3-butenyl-1-pyrophosphoric acid, phosphohalohydrins, phosphoepoxides etc. may be used. The concentration of the components in a medium is not particular limited as long as the desired effect is obtained.

Further, serum or plasma can be also added to the medium. The amount of serum or plasma to be added to the medium is not particularly limited, and it is more than 0 to 20% by volume, preferably more than 0 to 10% by volume. For example, autologous-derived serum or plasma can be used.

A cell culture instrument used for culture is not particularly limited, and for example, a petri dish, a flask, a bag, a bioreactor etc. can be used. As the bag, for example, a $CO_2$ gas permeable bag for cell culture can be used. When a large amount of lymphocytes are prepared industrially, use of a bioreactor is advantageous. Although culture can be performed in either of an open system or a closed system, it is preferable to perform culture in a closed system from a view point of safety of the resulting lymphocyte.

Culture may be performed under known culture conditions, and the conditions which are used in normal cell culture can be applied. For example, culture can be performed under the conditions of 37° C., 5% $CO_2$ etc. Cells can be diluted by adding a fresh medium to a cell culture liquid at a suitable time interval, a medium can be exchanged with a fresh medium, or a cell culture instrument can be exchanged. A medium to be used, other components to be used at the same time etc. can be appropriately selected depending on the kind of a lymphocyte to be prepared, as described later. A culture period is, for example, 1 to 40 days, preferably 2 to 35 days, more preferably 3 to 30 days, and a culture period of 3 to 25 days is preferable from a view point of realizing a higher expansion culturing rate.

Components including the polypeptide having an amino acid sequence derived from fibronectin used in the culture may be dissolved and present in a medium, or may be immobilized on a suitable solid phase, for example, a carrier for cell culture such as a cell culture instrument, a bead, a membrane, or a slide glass. For example, immobilization of an anti-CD3 antibody can be performed according to the method described in WO 97/18318, and immobilization of the polypeptide having an amino acid sequence derived from fibronectin can be performed according to the method described in WO 00/09168.

For the treatment of diminishing the proliferation ability, an anti-cancer agent, for example, mitomycin C can be used. The condition for anti-cancer agent treatment is not particularly limited as long as the proliferation ability of a treated cell is lost or reduced. The concentration of a mitomycin C is, for example, 1 to 100 µg/mL, preferably 2 to 50 µg/mL, suitably 5 to 30 µg/mL. A treatment temperature is, for example, 30 to 40° C., preferably 35 to 38° C. A treatment time is, for example, 0.1 to 2 hours, preferably 0.5 to 1 hour.

When the treatment of diminishing the proliferation ability is performed by irradiation of radiation such as a γ-ray or an X-ray, the irradiation amount of radiation is not particularly limited as long as the proliferation ability of an irradiated cell is lost, and for example, the amount is 100 to 20000 R (0.88 to 176 Gy), preferably 1000 to 8000 R (8.8 to 70 Gy).

When the treatment of diminishing the proliferation ability is performed by a mild heat treatment, a treating temperature and a treating time are not particularly limited as long as the proliferation ability of a cell is lost. The treating temperature is for example 40 to 55° C., preferably 42 to 50° C., and the treating time is for example 0.1 to 8 hours, preferably 0.2 to 4 hours.

In culture of a cell population containing a NK cell and/or a cell capable of differentiating into a NK cell, the cell concentration of the cell which has been subjected to a treatment of diminishing the proliferation ability is not particularly limited, and it is, for example, 1 to $1\times10^8$ cells/mL, preferably $1\times10^1$ to $5\times10^7$ cells/mL, further preferably $1\times10^2$ to $2\times10^7$ cells/mL.

The process of the present invention is characterized by expansion-culturing a cell population containing a NK cell and/or a cell capable of differentiating into a NK cell in the presence of a bioresponse modifying agent and a cell which has been subjected to a treatment diminishing the proliferation ability.

In the present invention, a cell population containing a NK cell and/or a cell capable of differentiating into a NK cell is used. Herein, the cell capable of differentiating into a NK cell is not particularly limited as long as the cell has the ability to differentiate into a NK cell. As the cell population, a body fluid such as peripheral blood, a bone marrow fluid, umbilical blood, or a lymph fluid, or a cell population separated from the body fluid, or each body part or organ (e.g. PBMC, umbilical blood mononuclear cell, bone marrow cell, hematopoietic stem cell etc.) can be used in the present invention. As the cell or the cell population, a cell or a cell population collected from a living body can be used directly or after freezing preservation. Further, a cell population obtained from the cell population via various derivation operations or separation operations, for example, a cell subset separated from cells such as PBMC based on a particular cell surface marker, for example, an isolated NK cell population or a cell population from which CD3-positive cells have been removed, can be also used in the present invention. In addition, a purified NK cell population or NK cell strain can be used in the present invention. The process of the present invention is characterized, for example, in that even when culture is directly initiated from PBMC having a low content of a NK cell, a cell population having a high NK cell content and having strong cytotoxic activity can be effectively obtained.

A period for culturing a cell population containing a NK cell and/or a cell capable of differentiating into a NK cell in the process of the present invention is, for example, 3 to 40 days, preferably 5 to 35 days, more preferably 10 to 30 days and, from a view point of realizing a higher expansion culturing rate, a culturing period of 14 to 25 days is preferable.

In culture of a cell population containing a NK cell and/or a cell capable of differentiating into a NK cell, the concentration of the NK cell and/or the cell capable of differentiating into a NK cell is not particularly limited, and it is for example 1 to $1\times10^8$ cells/mL, preferably $1\times10^1$ to $5\times10^7$ cells/mL, further preferably $1\times10^2$ to $2\times10^7$ cells/mL. The ratio of the cell number of the cell population containing a NK cell and/or a cell capable of differentiating into a NK cell to the cell number of a cell population which has been subjected to a treatment of diminishing the proliferation ability is not particularly limited, and it is, for example, 1:0.1 to 20, preferably 1:1 to 10.

The cell population which has been subjected to a treatment of diminishing the proliferation ability is added to a medium at initiation of culture of the cell population containing a NK cell and/or a cell capable of differentiating into a NK cell. Further, the cell population containing a NK cell and/or a cell capable of differentiating into a NK cell is stimulated by adding the cell population which has been subjected to a treatment of diminishing the proliferation ability one or more times in addition to the culture initiation, for example, once, two times or three times during culturing, and thereby, an expansion culturing rate can be further improved. Without particular limitation, for example, the cell which has been subjected to a treatment of diminishing the proliferation ability may be added again at a preferable time between 5 to 9 days and/or at a preferable time between 11 to 15 days after culture initiation of the cell population containing a NK cell and/or a cell capable of differentiating into a NK cell. The cell population which has been subjected to a treatment of diminishing the proliferation ability may be freezing-preserved by a suitable method until use.

The bioresponse modifying agent which is another characteristic of the process of the present invention is not particularly limited as long as it has the desired NK cell proliferation inducing activity. In a preferable aspect, the bioresponse modifying agent used in the present invention may be a microorganism-derived preparation, and particularly preferably, OK-432, BCG, *Streptcoccus pyogenes*, *Corynebacterium parvum* or a cell wall skeleton thereof is used.

The amount of the bioresponse modifying agent to be added to a medium is not particularly limited, and it may be appropriately selected depending on the use amount of a cell to be subjected to expansion culture and the amount of the cell population which has been subjected to a treatment of diminishing the proliferation ability to be used together. When OK-432 is used, OK-432 is added to a medium at a final concentration of 0.001 to 1 KE/mL, preferably 0.005 to 0.5 KE/mL, further preferably 0.01 to 0.2 KE/mL, without particular limitation of the present invention. Usually, the bioresponse modifying agent may be added to a medium at culture initiation.

A medium used in the process of the present invention is not particularly limited expect for use of the bioresponse modifying agent and the cell which has been subjected to a treatment of diminishing the proliferation ability. A known medium suitable for culturing a lymphocyte can be used. For example, a commercially available culture medium a NK cell (CellGro SCGM of CellGenix, GT-T502 of TAKARA BIO INC. etc.) may be used. The medium may contain suitable proteins, cytokines or other components in addition to the active components of the present invention. Preferably, a medium containing IL-2 is used in the present invention. The concentration of IL-2 in the medium is not particularly limited, and it is, for example, 0.01 to $1 \times 10^5$ U/mL, preferably 0.1 to $1 \times 10^4$ U/mL.

Serum or plasma may be added to the medium. The amount of them to be added to the medium is not particularly limited, and it is more than 0 to 20% by volume, preferably more than 0 to 5% by volume. When a prepared cell population containing a NK cell or a cell subpopulation separated from the cell population is transferred into a living body, serum or plasma having the same origin (that is, derived from the same individual) as that of the NK cell and/or the cell capable of differentiating into a NK cell is preferably used. Also, blood-derived proteins, for example, serum albumin may be added to the medium. In this case, an isolated blood-derived protein, that is, a blood-derived protein substantially not containing other components derived from blood is preferably used. An available recombinant blood-derived protein may be also used.

During culture in the process of the present invention, dilution of a cell culture liquid, exchange of a medium or exchange of a cell culture instrument may be performed at a suitable time interval or depending on increase in the cell number.

In addition, the process of the present invention can be also performed according to the general conditions for culturing a NK cell or a LAK cell. For example, the process may be according to Klin Padiatr, 2005, vol. 217, p. 345-350; Journal of Experimental Medicine, 1982, vol. 155, p. 1823-1841; Current Protocols in Immunology, Supplement 17, UNIT 7.7.

The present invention further provides a process for preparing a cell population containing a natural killer cell, characterized by including a step of expansion-culturing an isolated and/or purified cell population containing a natural killer cell and/or a cell capable of differentiating into a natural killer cell, in the presence of a bioresponse modifying agent. For example, there is provided a process for preparing a cell population containing a natural killer cell comprising culturing a purified CD3-negative CD56-positive cell in the presence of OK-432. In the process, an expansion culturing rate of the cell population containing a natural killer cell is improved by culturing the cell population in the presence of a cell which has been subjected to a treatment of diminishing the proliferation ability.

2. A Cell Population Containing a NK Cell Obtained by the Process of the Present Invention, a Medicament Containing the Cell Population, Use of the Cell Population, and a Therapeutic Method or a Prophylactic Method Using the Cell Population Further, the present invention provides a cell population containing a NK cell obtained by the process for preparing a NK cell of the present invention, and a cell subpopulation separated from the cell population. Also, the present invention provides a medicament (therapeutic agent) containing the cell population and/or the cell subpopulation as an active ingredient, use of the cell population and/or the cell subpopulation for producing a medicament, as well as a method of treating or preventing a disease comprising a step of administering an effective amount of the cell population and/or the cell subpopulation to a subject.

The cell population and/or the cell subpopulation containing a NK cell obtained by the process of the present invention (hereinafter, simply referred to as the cell population of the present invention) has an extremely high content of a NK cell, extremely high cytotoxic activity including antibody-dependent cell-mediated cytotoxicity (ADCC), and extremely high the multifunction ability, as compared with a cell population obtained by a conventional method. Particularly, in the cell population of the present invention, CD3-negative (NK cell surface marker) CD56-positive (NK cell surface marker) cells account for at least 50% or more. The cell population of the present invention contains a high proportion of CD16-positive CD56-positive cells which have high cytotoxic activity. CD16-positive CD56-positive cells account for at least 50%, preferably 60% or more, more preferably 70% or more of the cell population. Further, the cell population of the present invention contains a high proportion of cells positive for CD94 and CD56 which are mature NK cells. CD94-positive CD56-positive cells account for at least 50%, preferably 60% or more, more preferably 70% or more of the cell population. The cell population of the present invention is a highly functional NK cell population containing a high proportion of cells expressing NKp44 and NKG2D which are said to be involved in cytotoxic activity of NK cells, NKp46 which is a surface antigen marker common to NK cells, CD25 expressed in an activated NK cell, CD62L involved in homing of a lymphocyte, CD69 which is also known as activation inducer molecule (AIM), expressed at an initial stage of activation of a leukocyte, and involved in target cytolysis action in a NK cell, or CXCR3 which is a ligand for CXCL9 and CXCL10 being a chemokine and is thought to exhibit the high ability to migrate to cancer cells expressing these chemokines or to accumulate in the cancer cells.

The multifunction ability of a NK cell generally allows production of a cytokine such as interferon (IFN)-γ or tumor necrosis factor (TNF)-α, or assessment of immune response of a cell population by a cell surface antigen such as CD107a. The cell population containing a NK cell prepared by the present invention contains a high proportion of cells producing plural cytokines or exhibiting plural cell surface antigens, and is extremely useful in cell immunotherapy as a multifunctional cell population having the multifunction ability.

The cytotoxicity of the cell population of the present invention can be enhanced by coexistence of the cell population of the present invention with a suitable cytokine, for example, interferon α (IFN-α). Such treated cell population can exert cytotoxicity against various cancer cells.

A gene may be transferred into the cell population of the present invention. For example, a gene encoding a protein having affinity for a target substance [e.g. T cell receptor (TCR), antibody, receptor etc.], a cell surface antigen, an enzyme, a signal transduction molecule (e.g. cytokine), a functional domain thereof (e.g. a variable region of an antibody or TCR, a single-chain antibody, a signaling domain of a receptor), or a chimeric protein having the functional domain may be transferred. A method for transferring the gene is not particularly limited, and a suitable method can be selected from known gene transfer methods and can be used. As the gene transfer method, either a method with a virus vector or a method without the vector can be used in the present invention. Regarding details of such methods, many literatures have been already published.

The cell population of the present invention may be freezing-preserved. When the cell population of the present invention is frozen/thawed, the cell can be returned to a cell retaining cytotoxic activity before freezing by re-culturing the cell population after thawing. Culture of the cell population may be performed, for example, for one day (overnight). The cytotoxic ability can be further enhanced by coexistence of the cell with a suitable cytokine, for example, IL-2 in re-culturing.

Examples of the cell subpopulation separated from the cell population containing a NK cell of the present invention include a cell subpopulation separated from a NK cell using, as an index, at least one surface marker of a NK cell selected from the group consisting of CD16, CD56, NKp44, NKG2D, NKp46, CD25, CD62L, CD69, CXCR3 and CD94.

A medicament (therapeutic agent) containing the cell population of the present invention is suitable for use in adoptive immunotherapy. In adoptive immunotherapy, the cell population of the present invention suitable for treatment of a patient is, for example, intravenously administered to the patient. The medicament is very useful in use for diseases and donor lymphocyte transfusion described later. The medicament can be prepared according to a known method in the pharmaceutical field, for example, by mixing the cell population of the present invention as an active ingredient with known organic or inorganic carriers, excipients, stabilizers etc. which are suitable for parenteral administration. The content of the cell population of the present invention in the medicament, a dose of the medicament and various conditions with respect to the medicament can be appropriately determined according to a known adoptive immunotherapy, and are not particularly limited. For example, a dose of the medicament is preferably $1 \times 10^5$ to $1 \times 10^{12}$ cells/day, more preferably $5 \times 10^5$ to $5 \times 10^{11}$ cells/day, further preferably $1 \times 10^6$ to $1 \times 10^{11}$ cells/day per adult of the cell population of the present invention. Usually, the cell population containing a NK cell can be administered into a vein, an artery, a subcutis, an abdominal cavity, a tumor etc. by injection, drip infusion etc.

The medicament of the present invention can be also administered together with, for example, an ingredient which can function as a vaccine against a disease to be treated, without particular limitation. For example, for treatment of a cancer, a tumor antigen, a cell capable of presenting an antigen, an antigen-presenting cell, a cell derived from a tumor tissue which has lost the proliferation ability by an artificial operation, an extract from a tumor tissue etc. can be also administered.

In combination with administration of the medicament, a lymphocyte stimulating factor, for example, an anti-CD3 antibody, an anti-CD28 antibody, a cytokine (IL-2, IL-15, IL-7, IL-12, IFN-γ, IFN-α, IFN-β etc.), a chemokine etc. can be also appropriately administered. The medicament of the present invention may contain the cell population of the present invention treated with these lymphocyte stimulating factors, as an active ingredient. As used herein, the lymphocyte stimulating factor includes a lymphocyte growth factor.

Examples of diseases for which the cell population of the present invention is administered include, but not particularly limited to, malignant tumor diseases such as cancer and leukemia, hepatitis, influenza, and infectious diseases caused by a virus such as HIV, a bacterium or a fungus (e.g. tuberculosis, MRSA, VRE or deep mycosis). The cell population containing a NK cell prepared by the process of the present invention can be utilized in combination with conventional therapeutic methods such as infectious disease prevention after bone marrow transplantation or radiation, donor lymphocyte transfusion for the purpose of remission of relapsed leukemia, anti-cancer agent treatment, radiation treatment, antibody therapy, mild heat therapy, other immunotherapies etc.

Use of the cell population of the present invention in production of a medicament, for example, in production of a medicament for treating a cancerous disease or an infectious disease is also included in the present invention.

The cell population of the present invention for use in treatment of a disease is also included in the present invention.

As another aspect of the present invention, a method of treating a disease using the medicament is provided. The method of treating a disease is characterized by use of the cell population of the present invention, and various conditions for administration of the medicament can be determined according to a known adoptive immunotherapy or the disclosure herein of administration of the medicament.

The present invention will be explained further specifically and in detail below by way of Examples, which the present invention is not limited to.

EXAMPLES

Example 1

Culture of NK Cell Using OK-432 and Autologous-Irradiated Cell (AIC)

(1) Separation and Storage of PBMC

In a healthy human donor from whom informed consent had been obtained, blood collection for components was performed (herein, the blood collection for components is blood collection for the purpose of collecting a mononuclear cell). After the blood collected for components was diluted about 2-fold with Dulbecco PBS (manufactured by Invitrogen Corporation, or manufactured by NISSUI PHARMACEUTICAL CO., LTD.; hereinafter, referred to as DPBS) or a physiological saline containing 1% human serum albumin (product name Buminate: manufactured by Baxter, hereinafter, referred to as HSA) (hereinafter, referred to as 1% HSA/physiological saline), each 30 mL of the diluted blood collected for components was layered on 15 mL of Ficoll-Paque PREMIUM or Ficoll-Paque PLUS (both manufactured by GE Healthcare Bioscience), followed by centrifugation at 700×g and room temperature for 20 minutes. After centrifugation, of separated layers, a PBMC layer was recovered with a pipette, and filled up to 45 mL using a RPMI1640 medium or 1% HSA/physiological saline. After centrifugation at 650×g and 4° C. for 10 minutes, the supernatant was removed. Similarly, centrifugation operations were sequentially performed while centrifugation G was stepwisely fallen, such as 600×g and then 500×g, washing was repeated a total of three times, and PBMC was collected.

The collected PBMC was suspended in a storage liquid (hereinafter, referred to as CP1/HSA) consisting of a mixture of equal amounts of CP-1 (manufactured by Kyokuto Pharmaceutical Industrial Co., Ltd.) comprising 8% HSA and a RPMI1640 medium (manufactured by Invitrogen Corporation, manufactured by Sigma Corporation, or manufactured by Wako Pure Chemical Industries, Ltd.), and stored in liquid nitrogen. For expansion culture of a NK cell, the stored PBMC was rapidly thawed in a water bath at 37° C., and washed with a RPMI1640 medium comprising 10 μg/mL DNase (manufactured by Calbiochem) or GT-T551 (manufactured by TAKARA BIO INC.; hereinafter, referred to as 0.5HGT-T551) comprising 0.5% human type AB serum (manufactured by Lonza), and the number of live cells was calculated by a trypan blue staining method. This cell was subjected to each experiment.

(2) Preparation of PBMC AIC

A necessary amount of PBMC prepared in Example 1-(1) was suspended in a RPMI1640 medium containing 5% human type AB serum, 0.1 mM NEAA mixture, 1 mM sodium pyruvate, and 2 mM L-glutamine (all manufactured by Lonza), and 1% penicillin-streptomycin (manufactured by Gibco BRL) or 100 μg/mL streptomycin sulfate (manufactured by Meiji Co., Ltd.) (hereinafter, referred to as 5HRPMI), and then irradiated with an X-ray at 3400 R (29.8 Gy) using an X-ray irradiation apparatus (the cell after X-ray irradiation is hereinafter referred to as PBMC AIC). The prepared PBMC AIC was suspended in 5HRPMI to $2 \times 10^6$ cells/mL.

(3) Expansion Culture of NK Cell

After PBMC (derived from the same donor as that of PBMC AIC) prepared in Example 1-(1) was suspended in 5HRPMI to $2 \times 10^6$ cells/mL, this was used as a Responder cell. The Responder cell and PBMC AIC were added each in an amount of 0.5 mL/well to a 24-well cell culture plate (manufactured by Becton, Dickinson and Company, or manufactured by Corning Incorporated), to a total of 1 mL/well (AIC-stimulation group). At this time, a group with non-addition of PBMC AIC (AIC non-stimulation group) was prepared.

OK-432 (product name Picibanil: manufactured by Chugai Pharmaceutical Co., Ltd.) was added to each well in a final concentration of 0.05 KE/mL. IL-2 (product name Proleukin: manufactured by Chiron, or manufactured by Novartis) was added to all wells in a final concentration of 500 U/mL. Culture of these plates was initiated at 37° C. in the presence of 5% $CO_2$ (culture $0^{th}$ day). On second day, each 1 mL of 5HRPMI was added to each well, and IL-2 was added in a final concentration of 500 U/mL.

On fourth day, IL-2 was added to each well in a final concentration of 500 U/mL. On seventh day, and ninth day, a cell liquid of each well was 3-fold diluted using 5HRPMI, IL-2 was added to each well in a final concentration of 500 U/mL and, thereafter, 2 mL of the diluted cell liquid was transferred to a new 24-well cell culture plate. On eleventh day after culture initiation, the cell liquid was 4-fold diluted, 4 mL of the diluted cell liquid was transferred to a new 12-well cell culture plate (manufactured by Becton, Dickinson and Company, or manufactured by Corning Incorporated) and, thereafter, IL-2 was added in a final concentration of 500 U/mL. Culture was continued until fourteenth day after culture initiation. On fourteenth day after culture initiation, the number of live cells was measured by a trypan blue staining method and the number was compared with the cell number at culture initiation to calculate an expansion culturing rate. Results are shown in Table 1. In the following Table, "−" means no addition and "+" means addition. In Examples, AIC addition has the same meaning as that of AIC stimulation, and AIC non-addition has the same meaning as that of AIC non-stimulation.

TABLE 1

| AIC | Expansion culturing rate |
|---|---|
| − | ×11.6 |
| + | ×97.5 |

As shown in Table 1, the PBMC AIC-addition group (AIC-stimulation group) exhibited a higher expansion culturing rate by combining OK-432 and AIC, as compared with the PBMC AIC non-addition group (AIC non-stimulation group).

That is, it was made clear that a NK cell was obtained at a high expansion culturing rate by combining OK-432 and AIC in expansion culture.

(4) Analysis of CD3-Negative CD56-Positive Cell (NK Cell) Content Rate

Regarding the cells on fourteenth day after culture initiation prepared in Example 1-(3), a CD3-negative CD56-positive cell content rate (hereinafter, referred to as NK cell content rate) was analyzed with a flow cytometer (Cytomics FC500: manufactured by Beckman Coulter Inc.). That is, the cells on fourteenth day after culture initiation were washed with DPBS, and then suspended in DPBS containing 1% bovine serum albumin (manufactured by Sigma Corporation, hereinafter referred to as BSA) (hereinafter, referred to as 1% BSA/DPBS), and a FITC-labeled or PC5-labeled mouse anti-human CD3 antibody and RD1-labeled mouse anti-human CD56 antibody (all manufactured by Beckman Coulter Inc.) were added thereto. Similarly, FITC-labeled mouse IgG1/RD1-labeled mouse IgG1/PC5-labeled mouse IgG1 (manufactured by Beckman Coulter Inc.) as a negative control were added to a portion of each cell population. After each antibody was added, incubation was performed at 4° C. for 30 minutes. After incubation, the cells were washed with DPBS containing 0.1% BSA (hereinafter, referred to as 0.1% BSA/DPBS), and suspended again in DPBS. These cells were subjected to flow cytometry. A NK cell content rate was calculated, wherein a CD3-negative CD56-positive cell group was regarded as a NK cell. Results are shown in Table 2.

TABLE 2

| AIC | NK cell content rate (%) |
|---|---|
| − | 49.72 |
| + | 79.09 |

As shown in Table 2, a cell population having a higher NK cell content rate was obtained by culture in the presence of a combination of OK-432 and AIC, as compared with a PBMC AIC non-addition group.

(5) Measurement of Cytotoxic Activity

Regarding the cells on fourteenth day after culture initiation prepared in Example 1-(3), cytotoxic activity was measured. Cytotoxic activity was assessed by a cytotoxic activity measuring method using Calcein-AM [Lichtenfels R. et al., J. Immunol. Methods, vol. 172, No. 2, p. 227-239 (1994)]. That is, each of a chronic myelocytic leukemia cell strain K562 cell (Health Science Research Resources Bank JCRB0019), a Burkitt lymphoma cell strain Daudi cell (Health Science Research Resources Bank JCRB9071), and a Burkitt lymphoma cell strain Raji (Health Science Research Resources Bank IFO50046) was suspended in a RPMI1640 medium containing 5% bovine fetal serum at 1 to $2\times10^6$ cells/mL. Thereto, Calcein-AM (manufactured by DOJINDO LABORATORIES) was added in a final concentration of 25 μM, and cultured at 37° C. for 1 hour. After the cells were washed with a medium not containing Calcein-AM, this was adopted as Calcein-labeled target cell.

The cells on fourteenth day after culture initiation prepared in Example 1-(3), as an effector cell, were diluted with 5HRPMI to $1\times10^6$ cells/mL, $3\times10^5$ cells/mL or $1\times10^5$ cells/mL. Then, each 100 μL/well of the dilution was dispensed in each well of a 96-well cell culture plate (manufactured by Corning Incorporated). Thereto, $1\times10^5$ cells/mL of a Calcein-labeled target cell was added at 100 μL/well. At this time, the ratio of an effector cell (E) to a Calcein-labeled target cell (T), that is, E/T ratio was 10, 3 or 1. The plate containing the cell suspension was centrifuged at 400×g for 1 minute, and then incubated at 37° C. for 4 hours in the presence of 5% $CO_2$. Thereafter, 100 μL of the culture supernatant was collected from each well. The amount of Calcein released into the culture supernatant was measured with a fluorescent plate reader (Mithras LB 940: manufactured by Berthold) (excitation 485 nm/measurement 535 nm). "Cytotoxic activity (%)" was calculated according to the following equation (1).

[Mathematic 1]

$$\text{Cytotoxic activity}(\%) = [\{(\text{measured value of each well}) - (\text{minimum release amount})\} / \{(\text{maximum release amount}) - (\text{minimum release amount})\}] \times 100 \quad \text{Equation (1)}$$

In the above equation, the minimum release amount is the Calcein release amount in a well containing only a Calcein-labeled target cell, and shows the amount of Calcein spontaneously released from a Calcein-labeled target cell. The maximum release amount shows the Calcein release amount when 0.1% surfactant Triton X-100 (manufactured by Nacalai Tesque, Inc.) is added to a Calcein-labeled target cell to completely destruct the cell. Results of measurement of cytotoxic activity are shown in Table 3.

TABLE 3

| AIC | E/T ratio | Cytotoxic activity (%) | | |
|---|---|---|---|---|
| | | K562 | Daudi | Raji |
| − | 10 | 82.15 | 75.24 | 59.83 |
| | 3 | 72.57 | 65.63 | 42.88 |
| | 1 | 58.97 | 44.65 | 21.98 |
| + | 10 | 70.49 | 80.01 | 52.34 |
| | 3 | 68.00 | 75.43 | 38.96 |
| | 1 | 57.70 | 56.76 | 19.05 |

As shown in Table 3, the cell population obtained by culture in the presence of a combination of OK-432 and AIC exerted cytotoxic activity equivalent to that of a cell population obtained without AIC.

That is, it was made clear that a cell population containing a NK cell which exerted high cytotoxic activity was effectively expanded and was obtained in a large amount by combining OK-432 and AIC in culture.

Example 2

Culture of NK Cell Using OK-432 and AIC
(Comparison of X-Ray Irradiation Amounts to AIC)

(1) Preparation of PBMC AIC PBMC AICs were prepared in the same manner as that of Example 1-(2) except that two kinds of PBMC AICs were prepared using an X-ray irradiation amount of 3400 R (29.8 Gy) and 8000 R (70.2 Gy), respectively.

(2) Expansion Culture of NK Cell

Expansion culture of a NK cell was performed in the same manner as that of Example 1-(3) except that an OK-432 non-addition group, a PBMC AIC non-addition group, and a group to which an equivalent amount of PBMC (X-ray unirradiated) in place of PBMC AIC was added were made. On seventh day after culture initiation, a cell liquid of each well was 2-fold diluted using 5HRPMI, IL-2 was added to each well in a final concentration of 500 U/mL and, thereafter, 2 mL of the cell liquid was transferred to a new 24-well cell culture plate. On ninth day and thirteenth day, the same subculturing operation was performed. The dilution rates of the cell liquids on ninth day and thirteenth day were 4-fold and 2-fold, respectively. On every subculturing day, IL-2 was added in a final concentration of 500 U/mL. Culture was continued until fourteenth day. The number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 4.

TABLE 4

| OK-432 | AIC (X-ray irradiation amount) | Expansion culturing rate | NK cell content rate (%) |
|---|---|---|---|
| − | − | ×5.78 | 7.25 |
| − | + (3400R) | ×10.13 | 28.02 |
| − | + (8000R) | ×6.30 | 9.59 |
| + | − | ×9.63 | 52.34 |
| + | −* | ×11.47 | 76.03 |
| + | + (3400R) | ×31.20 | 85.86 |
| + | + (8000R) | ×27.80 | 87.30 |

*PBMC which has not been irradiated with X-ray is added as a control, and AIC is not added.

As shown in Table 4, an expansion culturing rate when OK-432 and PBMC AIC were combined was higher as compared with an OK-432 non-addition group, a PBMC AIC non-addition group and a PBMC (without X-ray irradiation)-addition group. The NK cell content rate in the resulting cell population when OK-432 and PBMC AIC were combined was also higher. Further, regardless of the X-ray irradiation amount used in PBMC AIC preparation, the effect was exerted. That is, it was made clear that a cell population containing a high proportion of a NK cell was obtained at a high expansion culturing rate by combining OK-432 and AIC in culture.

Example 3

Culture of NK Cell Using OK-432 and Various AICs (Comparison Between PBMC AIC and RN-T AIC)

(1) Preparation of Anti-human CD3 Antibody and RetroNectin-immobilized Plate

Each 0.45 mL/well of an ACD-A liquid (manufactured by TERUMO CORPORATION) containing a final concentration of 5 µg/mL of an anti-human CD3 antibody (product name: Orthoclone OKT3 injection, manufactured by Janssen Pharmaceutical K.K.) and a final concentration of 25 µg/mL of RetroNectin (registered trademark name, manufactured by TAKARA BIO INC.) was added to 12-well cell culture plates to obtain the necessary number of wells. The plates were incubated at 37° C. for 5 hours in the presence of 5% $CO_2$. The anti-CD3 antibody/RetroNectin-immobilized plate was washed two times with DPBS, and once with a RPMI1640 medium immediately before use.

(2) Expansion Culture of Anti-CD3 Antibody/RetroNectin-stimulated T Cell

The PBMC prepared in Example 1-(1) was suspended in GT-T551 (manufactured by TAKARA BIO INC.) containing 1% human type AB serum (manufactured by Lonza) (hereinafter, referred to as 1HGT-T551) at $1 \times 10^6$ cells/mL. To the anti-human CD3 antibody/RetroNectin-immobilized plates prepared in Example 3-(1) was added 4.77 mL/well of 1HGT-T551, and each 0.53 mL/well of the cell suspension was added to the plates to make the necessary number of wells. Subsequently, IL-2 was added to each well in a final concentration of 200 U/mL. Culture of these plates was initiated at 37° C. in the presence of 5% $CO_2$ (culture $0^{th}$ day). On fourth day after culture initiation, the culture liquid was appropriately diluted using 1HGT-T551 and, thereafter, transferred to a T75 cell-culture flask (manufactured by Corning Incorporated). IL-2 was added to this flask in a final concentration of 200 U/mL, and culture was continued until seventh day (hereinafter, a T cell obtained by expansion culture with anti-CD3 antibody/RetroNectin stimulation is referred to as RN-T).

(3) Preparation of AIC Using PBMC and RN-T

AIC was prepared in the same manner as that of Example 1-(2) except that each of PBMC prepared in the same manner as that of Example 1-(1) and RN-T on seventh day after culture initiation prepared in Example 3-(2) was irradiated with an X-ray at 3400 R (29.8 Gy) for preparation of AIC (hereinafter, this RN-T after X-ray irradiation is referred to as RN-T AIC). The prepared PBMC AIC and RN-T AIC were suspended in CellGro SCGM (manufactured by CellGenix) containing 1% human type AB serum (hereinafter, referred to as 1HCellGro) or CellGro containing 5% human type AB serum (hereinafter, referred to as 5HCellGro) at $2 \times 10^6$ cells/mL, and the suspensions were used in the following experiment.

(4) Expansion Culture of NK Cell Population

Expansion culture of a NK cell was performed in the same manner as that of Example 1-(3) except that 1HCellGro or 5HCellGro was used as a culture medium and PBMC AIC and RN-T AIC prepared in Example 3-(3) were used as AIC.

On second day after culture initiation, each 1 mL of 1HCellGro or 5HCellGro was added to each well, and IL-2 was added in a final concentration of 200 U/mL. On fifth day, IL-2 was added to each well in a final concentration of 200 U/mL. On seventh day, a cell liquid of each well was 3-fold diluted using 1HCellGro or 5HCellGro, and 2 mL of the diluted cell liquid was transferred to a new 24-well cell culture plate. On ninth day and thirteenth day, the same subculturing operation was performed. The dilution rates of the cell liquids on ninth day and thirteenth day were 5-fold and 4-fold, respectively. In this manner, culture was continued until sixteenth day after culture initiation. On every subculturing day, IL-2 was added to each well in a final concentration of 200 U/mL. On sixteenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 5.

TABLE 5

| Culture medium | OK-432 | AIC used | Expansion culturing rate | NK cell content rate (%) |
|---|---|---|---|---|
| 5HCellGro | + | PBMC AIC | ×129.8 | 96.2 |
|  | + | RN-T AIC | ×121.5 | 98.4 |
| 1HCellGro | + | PBMC AIC | ×144.0 | 97.5 |
|  | + | RN-T AIC | ×163.5 | 98.8 |

As shown in Table 5, an equivalent expansion culturing rate was obtained by use of RN-T AIC, as compared with a PBMC AIC-addition group. No difference was seen in the NK cell content rates of the resulting cell populations. That is, it was made clear that a cell population containing a high proportion of a NK cell was effectively obtained, regardless of the serum concentration in a culture medium, by combining OK-432 and PBMC AIC or RN-T AIC in culture of a NK cell. Thus, an expansion culturing method using a low serum concentration was established.

Example 4

Culture of NK Cell Using OK-432 and Various AICs (Re-Stimulation with AIC-1)

(1) Preparation of Anti-Human CD3 Antibody and RetroNectin-immobilized Plate

In the same manner as that of Example 3-(1), an anti-human CD3 antibody and RetroNectin-immobilized plate was prepared.

(2) Expansion Culture of Anti-CD3 Antibody/RetroNectin-stimulated T Cell

Expansion culture of RN-T was performed in the same manner as that of Example 3-(2) except that a culture period was 19 days, cells were appropriately diluted using 1HGT-T551 on fourth day after culture initiation or thereafter, and IL-2 was added in a final concentration of 200 U/mL on every subculturing day to continue the culture.

(3) Preparation of RN-T AIC

In the same manner as that of Example 3-(3), AIC was prepared. The RN-T cultured in Example 4-(2) was recovered on sixth, thirteenth and nineteenth days after culture initiation and irradiated with an X-ray at 3400 R (29.8 Gy) using an X-ray irradiating apparatus. The cells were suspended in 1HCellGro, and used in the following experiment.

(4) Expansion Culture of NK Cell Population

Expansion culture of a NK cell was performed in the same manner as that of Example 1-(3) except that 1HCellGro was used as a culture medium and each RN-T AIC prepared in Example 4-(3) was used as AIC.

On second day after culture initiation, each 1 mL of 1HCellGro was added to each well, and IL-2 was added in a final concentration of 200 U/mL.

On fifth day, IL-2 was added to each well in a final concentration of 200 U/mL. On seventh day, a cell liquid of each well was 3-fold diluted using 1HCellGro, and 2 mL of the diluted cell liquid was transferred to a new 24-well cell culture plate. On ninth, thirteenth, sixteenth and twentieth days, the same subculturing operation was performed. The dilution rates of the cell liquids on ninth, thirteenth, sixteenth and twentieth days were 5-fold, 3-fold, 5-fold and 2-fold, respectively. On every subculturing day, IL-2 was added to each well in a final concentration of 200 U/mL. On seventh and thirteenth days after culture initiation, each $1\times10^6$ cells/well of each RN-T AIC prepared in Example 4-(3) was added. On sixteenth day, twentieth day and twenty-second day after culture initiation, the number of live cells was measured by a trypan blue staining method, and the number was compared with the cell number at culture initiation to calculate an expansion culturing rate. Results are shown in Table 6.

TABLE 6

| OK-432 | AIC | | | Expansion culturing rate | | |
|---|---|---|---|---|---|---|
| | $0^{th}$ day after culture initiation | $7^{th}$ day after culture initiation | $13^{th}$ day after culture initiation | $16^{th}$ day after culture initiation | $20^{th}$ day after culture initiation | $22^{nd}$ day after culture initiation |
| + | + | − | − | 69.30 | 413.44 | 450.00 |
| + | + | + | − | 97.65 | 523.13 | 702.00 |
| + | + | + | + | 159.08 | 635.63 | 823.50 |

As shown in Table 6, high NK cell expansion culturing rates were obtained on sixteenth day, twentieth day and twenty-second day after culture initiation by combining with RN-T AIC-stimulation in a NK cell expansion culture period.

As frequencies of stimulation with RN-T AIC in NK cell culture period were increased, a higher NK cell expansion culturing rate was obtained.

That is, it was made clear that proliferation ability of a NK cell was increased by stimulation with AIC. Therefore, it was made clear that, a NK cell was obtained at a high expansion culturing rate by combining with RN-T AIC in culture of a NK cell.

Example 5

Culture of NK Cell Using OK-432 and Various AICs (Re-stimulation with AIC-2)

(1) Preparation of Anti-Human CD3 Antibody and RetroNectin-immobilized Plate

In the same manner as that of Example 3-(1), an anti-human CD3 antibody and RetroNectin-immobilized plate was prepared.

(2) Expansion Culture of Anti-CD3 Antibody/RetroNectin-stimulated T Cell

In the same manner as that of Example 4-(2), expansion culture of RN-T was performed.

(3) Preparation of RN-T AIC

In the same manner as that of Example 3-(3), AIC was prepared. The RN-Ts recovered on seventh and fourteenth days after culture initiation in Example 5-(2) were irradiated with an X-ray at 3400R (29.8 Gy) using an X-ray irradiating apparatus, suspended in 5HCellGro, and used in the following experiment.

(4) Expansion Culture of NK Cell Population

Expansion culture of a NK cell was performed in the same manner as that of Example 1-(3) except that 5HCellGro was used as a culture medium and each RN-T AIC prepared in Example 5-(3) was used as AIC.

On second day after culture initiation, each 1 mL of 5HCellGro was added to each well, and IL-2 was added in a final concentration of 200 U/mL.

On fifth day, IL-2 was added to each well in a final concentration of 200 U/mL. On seventh day, a cell liquid of each well was 3-fold diluted using 5HCellGro, and 2 mL of the diluted cell liquid was transferred to a new 24-well cell culture plate. The same subculturing operation was performed on ninth day, thirteenth day, sixteenth day and twentieth day, and culture was continued until twenty-second day. The dilution rates of the cell liquids on ninth, thirteenth, sixteenth and twentieth days were 3-fold, 2.5-fold, 4-fold and 2-fold, respectively. On every subculturing day, each 1 mL of 5HCellGro was added to each well, and IL-2 was added in a final concentration of 200 U/mL. On seventh day, each $1\times10^6$ cells/well of the RN-T AIC prepared in Example 5-(4) was added. On twentieth day and twenty-second day after culture initiation, the number of live cells was measured by a trypan blue staining method, and the number was compared with the cell number at culture initiation to calculate an expansion culturing rate. Results are shown in Table 7.

TABLE 7

| OK-432 | AIC | | Expansion culturing rate | |
|---|---|---|---|---|
| | $0^{th}$ day after culture initiation | $7^{th}$ day after culture initiation | $20^{th}$ day after culture initiation | $22^{nd}$ day after culture initiation |
| + | + | − | 470.25 | 589.50 |
| + | + | + | 576.00 | 1030.50 |

As shown in Table 7, a higher expansion culturing rate was obtained by performing restimulation with RN-T AIC during NK cell expansion culture, as compared with the group which had not been subjected to the restimulation.

That is, it was made clear that, a NK cell was obtained at a high expansion culturing rate by combining OK-432 and a plurality of times of stimulation with RN-T AIC in culture of a NK cell.

(5) Analysis of CD3-negative CD56-positive Cell Content Rate (NK Cell)

In the same manner as that of Example 1-(4), the regarding cells on twenty-second day after culture initiation, prepared in Example 5-(4), a NK cell content rate was measured. Results are shown in Table 8.

TABLE 8

| OK-432 | AIC | | NK cell content rate (%) |
|---|---|---|---|
| | $0^{th}$ day after culture initiation | $7^{th}$ day after culture initiation | |
| + | + | − | 94.6 |
| + | + | + | 98.1 |

As shown in Table 8, a high NK cell content rate equivalent to that of a group which had not been subjected to the restimulation was obtained by giving restimulation with RN-T AIC during NK cell expansion culture. That is, even when a plurality of times of stimulation with RN-T AIC was given, a NK cell content rate was not reduced.

(6) Measurement of Cytotoxic Activity

Regarding the cells on twenty-second day after culture initiation prepared in Example 5-(4), cytotoxic activity was measured in the same manner as that of Example 1-(5) except that K562 and Daudi were used as target cells. Results of measurement of cytotoxic activity are shown in Table 9.

TABLE 9

| | AIC | | | Cytotoxic activity (%) | |
|---|---|---|---|---|---|
| OK-432 | 0th day after culture initiation | 7th day after culture initiation | E/T ratio | K562 | Daudi |
| + | + | − | 10 | 56.23 | 66.90 |
| | | | 3 | 49.32 | 52.41 |
| | | | 1 | 36.65 | 33.09 |
| + | + | + | 10 | 66.74 | 81.02 |
| | | | 3 | 70.11 | 66.45 |
| | | | 1 | 50.63 | 44.91 |

As shown in Table 9, it was made clear that higher cytotoxic activity was given to a cell group which had been stimulated with RN-T AIC again during NK cell expansion culture than a group which had been stimulated with RN-T AIC only on 0th day after culture initiation.

That is, it was made clear that, a cell population containing a NK cell exerting higher cytotoxic activity was effectively obtained by combining OK-432 with a plurality of times of stimulation with RN-T AIC in culture of a NK cell.

Example 6

Culture of NK Cell Using OK-432 and Various AICs (Comparison of X-Ray Irradiation Amounts)

(1) Preparation of Anti-Human CD3 Antibody and RetroNectin-immobilized Plate

In the same manner as that of Example 3-(1), an anti-human CD3 antibody and RetroNectin-immobilized plate was prepared.

(2) Expansion Culture of Anti-CD3 Antibody/RetroNectin-stimulated T Cell

Expansion culture of RN-T was performed in the same manner as that of Example 4-(2) except that a culture period was 14 days.

(3) Preparation of RN-T AIC

In the same manner as that of Example 3-(3), AIC was prepared. The RN-Ts which recovered on seventh day and fourteenth day after culture initiation in Example 6-(2) were irradiated with an X-ray at 1000 R (8.8 Gy), 2000 R (17.6 Gy), 3400 R (29.8 Gy) or 5500 R (48.2 Gy) using an X-ray irradiating apparatus, suspended in 5HCellGro, and used in the following experiment.

(4) Expansion Culture of NK Cell Population

Expansion culture of a NK cell was performed, in the same manner as that of Example 1-(3) except that 5HCellGro was used as a culture medium and each RN-T AIC prepared in Example 6-(3) was used as AIC.

On first day and third day after culture initiation, each 1 mL of 5HCellGro was added to each well, and IL-2 was added in a final concentration of 200 U/mL.

On fourth day or fifth day, IL-2 was added to each well in a final concentration of 200 U/mL. On seventh day, a cell liquid of each well was 9-fold diluted using 5HCellGro, 2 mL of the diluted cell liquid was transferred to a new 24-well cell culture plate, and each 1×10⁶ cells/well of the RN-T AIC prepared in Example 6-(3) was added. The aforementioned subculturing operation comprising diluting a cell liquid and transferring 2 mL of the diluted cell liquid to a new plate was performed on eleventh day, fourteenth day, fifteenth day, seventeenth day or eighteenth day, and culture was continued until twenty-first day after culture initiation. The dilution rates of the cell liquids on eleventh, fourteenth, fifteenth, seventeenth and eighteenth days were 5-fold, 3-fold, 4-fold, 4-fold and 2-fold, respectively. On every subculturing day, IL-2 was added to each well in a final concentration of 200 U/mL. On seventh day, each 1×10⁶ cells/well of the RN-T AIC prepared in Example 6-(3) was added. On twenty-first day after culture initiation, the number of live cells was measured by a trypan blue staining method, and the number was compared with the cell number at culture initiation to calculate an expansion culturing rate. Results are shown in Table 10.

TABLE 10

| Exp. | OK-432 | X-ray irradiation amount for preparation of AIC | AIC 0th day after culture initiation | 7th day after culture initiation | Expansion culturing rate 21st day after culture initiation |
|---|---|---|---|---|---|
| Exp. 1 | + | 1000R | + | − | 105.30 |
| | | | | + | 440.10 |
| | | 2000R | | − | 99.90 |
| | | | | + | 396.90 |
| | | 3400R | | − | 81.00 |
| | | | | + | 436.05 |
| Exp. 2 | + | 2000R | + | − | 436.5 |
| | | | | + | 499.5 |
| | | 5500R | | − | 333.0 |
| | | | | + | 463.5 |

As shown in Table 10, a higher NK cell expansion culturing rate was obtained by giving restimulation with RN-T AIC during NK cell expansion culture, as compared with a group which had not been subjected to the restimulation. Even when the X-ray irradiation amount for preparation of RN-T AIC was changed to 1000, 2000, 3400 or 5500 R, the effect was exerted.

That is, it was made clear that, a NK cell was obtained at a high expansion culturing rate even by combining with RN-T AICs prepared using different X-ray irradiation amounts in culture of a NK cell.

(5) Analysis of CD3-Negative CD56-Positive Cell (NK Cell) Content Rate

In the same manner as that of Example 1-(4), regarding the cells on twenty-first day after culture initiation prepared in Example 6-(4), a NK cell content rate was measured. Results are shown in Table 11.

TABLE 11

| Exp. | OK-432 | X-ray irradiation amount for preparation of AIC | AIC 0th day after culture initiation | 7th day after culture initiation | NK cell content rate (%) 21st day after culture initiation |
|---|---|---|---|---|---|
| Exp. 1 | + | 1000R | + | − | 93.87 |
| | | | | + | 98.55 |
| | | 2000R | | − | 96.52 |
| | | | | + | 98.80 |
| | | 3400R | | − | 95.18 |
| | | | | + | 98.26 |
| Exp. 2 | + | 2000R | + | − | 98.88 |
| | | | | + | 99.17 |
| | | 5500R | | − | 98.97 |
| | | | | + | 98.65 |

As shown in Table 11, a group in which had been stimulated with RN-T AIC again during NK cell expansion culture had a high NK cell content rate equivalent to that of a group which had not been stimulated at all. Even when the X-ray irradiation amount for preparation of RN-T AIC was changed to 1000, 2000, 3400 or 5500 R, the effect was exerted.

That is, it was made clear that, a cell population containing a high proportion of a NK cell was obtained at a high content rate by combining OK-432 and AIC in culture of a NK cell.

Example 7

Culture of NK Cell Using OK-432 and AIC
(Comparison of Basal Culture Medium-1)

(1) Preparation of AIC Using PBMC

In the same manner as that of Example 1-(2), PBMC AIC was prepared.

(2) Expansion Culture of NK Cell

Expansion culture of a NK cell was performed in the same manner as that of Example 1-(3) except that as a basal culture medium, GT-T503 (manufactured by TAKARA BIO Inc.) containing 5HRPMI, 5% human type AB serum and 0.2% HSA (hereinafter, referred to as 5H0.2% HSA/GT-T503) or 5HCellGro was used.

On seventh day after culture initiation, a cell liquid of each well was 3-fold diluted using each basal culture medium, IL-2 was added to each well in a final concentration of 200 U/Ml and, thereafter, 2 mL of the diluted cell liquid was transferred to a new 24-well cell culture plate. On ninth day, 2 mL of the cell liquid which had been 3-fold diluted similarly was transferred to a new 24 cell culture plate. Further, on eleventh day, 4 mL of the cell liquid which had been 5-fold diluted was transferred to a new 12-well cell culture plate. On every subculturing day, IL-2 was added to each well in a final concentration of 200 U/mL. Culture was continued until fifteenth day after culture initiation. On fifteenth day after culture initiation, the number of live cells was measured by a trypan blue staining method, and the number was compared with the cell number at culture initiation to calculate an expansion culturing rate. Results are shown in 12.

TABLE 12

| Basal culture medium | OK-432 | AIC | Expansion culturing rate (15$^{th}$ day after culture initiation) |
|---|---|---|---|
| 5HRPMI | + | + | ×9.56 |
| 5H0.2% HSA/GT-T503 | + | + | ×44.51 |
| 5HCellGro | + | + | ×80.37 |

As shown in Table 12, when OK-432, PBMC AIC and CellGro were combined, a higher expansion culturing rate was obtained as compared with other media.

(3) Analysis of CD3-Negative CD56-Positive Cell (NK Cell) Content Rate

Regarding the cells on fifteenth day after culture initiation prepared in Example 7-(2), a NK cell content rate was analyzed in the same manner as that of Example 1-(4). Results are shown in Table 13.

TABLE 13

| Basal culture medium | OK-432 | AIC | NK cell content rate (%) (15$^{th}$ day after culture initiation) |
|---|---|---|---|
| 5HRPMI | + | + | 82.90 |
| 5H0.2% HSA/GT-T503 | + | + | 71.38 |
| 5HCellGro | + | + | 87.52 |

As shown in Table 13, a cell population containing 70% or more of a NK cell was obtained using any medium. However, among used media, a group using CellGro had the highest NK cell content rate.

Example 8

Culture of NK Cell Using OK-432 and AIC
(Comparison of Basal Culture Medium-2)

(1) Preparation of Anti-Human CD3 Antibody and RetroNectin-Immobilized Plate

In the same manner as that of Example 3-(1), an anti-human CD3 antibody and RetroNectin-immobilized plate was prepared.

(2) Expansion Culture of Anti-CD3 Antibody/RetroNectin-Stimulated T-Cell

In the same manner as that of Example 6-(2), expansion culture of RN-T was performed.

(3) Preparation of AIC Using RN-T

Using the RN-T prepared in Example 8-(2), AIC was prepared in the same manner as that of Example 5-(3) except that RN-T AIC after X-ray irradiation was suspended in 1HCellGro; GT-T502 (manufactured by TAKARA BIO Inc.) containing 1% human type AB serum (hereinafter, referred to as 1HGT-T502); or GT-T503 (manufactured by TAKARA BIO Inc.) containing 1% human type AB serum and 0.2% HSA (hereinafter, referred to as 1H0.2% HSA/GT-T503), and used in the following experiment.

(4) Expansion Culture of NK Cell Population

Expansion culture of a NK cell was performed in the same manner as that of Example 1-(3) except that 1HCellGro was used at culture initiation as a basal culture medium, and on seventh day or ninth day after culture initiation and thereafter, the medium in some groups was changed to 1HGT-T502 or 1H0.2% HSA/GT-T503. Also, a group in which the medium was changed to 1HGT-T502 on fourteenth day after culture initiation and, a group in which a basal medium obtained by mixing 1HCellGro and 1HGT-T502 at a ratio of 1:1 (hereinafter, referred to as 1HCellGro/GT-T502) was used from culture initiation to culture end were set.

On fourth day after culture initiation, IL-2 was added to each well in a final concentration of 200 U/mL. On seventh day, a cell liquid of each well was 3-fold diluted using each a culture medium, and 2 mL of the cell liquid was transferred to a new 24-well cell culture plate. The same subculturing was performed on ninth day, fourteenth day and eighteenth day, and culture was continued until twenty-second day. The dilution rates of the cell liquids on ninth, fourteenth and eighteenth days were 5-fold, 3-fold and 2-fold, respectively. On every subculturing day, IL-2 was added to each well in a final concentration of 200 U/mL. On seventh day after culture initiation, each 1×10$^6$ cells/well of the RN-T AIC prepared in Example 8-(3) was added.

On fourteenth day, eighteenth day and twenty-first day after culture initiation, the number of live cells was measured by a trypan blue staining method, and the number was compared with cell number at culture initiation to calculate an expansion culturing rate. Results are shown in Table 14.

TABLE 14

| Basal medium at culture initiation | Change of basal medium | Basal medium after change | Expansion culturing rate(%) | | |
|---|---|---|---|---|---|
| | | | 14$^{th}$ day after culture initiation | 18$^{th}$ day after culture initiation | 21$^{st}$ day after culture initiation |
| 1HCellGro | None | | 53.55 | 151.31 | 278.78 |
| 1HCellGro/GT-T502 | None | | 43.05 | 138.94 | 311.85 |
| 1HCellGro | 7$^{th}$ day after culture initiation | 1HGT-T502 | 49.88 | 126.00 | 382.73 |
| | | 1H0.2% HSA/GT-T503 | 57.23 | 121.50 | 288.23 |
| | 9$^{th}$ day after culture initiation | 1HGT-T502 | 56.18 | 123.19 | 324.45 |
| | | 1H0.2% HSA/GT-T503 | 58.54 | 141.19 | 326.03 |
| | Culturing initiation 14$^{th}$ day | 1HGT-T502 | 51.98 | 151.31 | 373.28 |

As shown in Table 14, a high expansion culturing rate was obtained on fourteenth, eighteenth and twenty-first days after culture initiation by combining OK-432, RN-T AIC and CellGro at an initial stage of NK cell expansion culture, even when a basal medium was changed during a culture period. Even when a mixed medium (diluted CellGro) consisting of two kinds of basal media such as 1HCellGro/GT-T502 was used, a high expansion culturing rate was obtained similarly.

(5) Analysis of CD3-negative CD56-positive Cell (NK Cell) Content Rate

Regarding the cells on twenty-first day after culture initiation prepared in Example 8-(4), a NK cell content rate was analyzed in the same manner as that of Example 1-(4). Results are shown in Table 15.

TABLE 15

| Basal medium at culture initiation | Change of basal medium | Basal medium after change | NK cell content rate (%) | |
|---|---|---|---|---|
| | | | 14$^{th}$ day after culture initiation | 21$^{st}$ day after culture initiation |
| 1HCellGro | None | | 93.89 | 97.91 |
| 1HCellGro/GT-T502 | None | | 83.74 | 95.92 |
| 1HCellGro | 7$^{th}$ day after culture initiation | 1HGT-T502 | 85.47 | 97.46 |
| | | 1H0.2% HSA/GT-T503 | 88.02 | 95.94 |
| | 9$^{th}$ day after culture initiation | 1HGT-T502 | 87.83 | 97.89 |
| | | 1H0.2% HSA/GT-T503 | 91.95 | 97.64 |
| | 14$^{th}$ day after culture initiation | 1HGT-T502 | 94.52 | 98.01 |

As shown in Table 15, a high NK cell content rate was obtained on fourteenth day, eighteenth day and twenty-first day after culture initiation by combining OK-432, RN-T AIC and CellGro at an initial stage of NK cell expansion culture, even when a basal medium was changed during a culture period. Also when a mixed medium (diluted CellGro) consisting of two kinds of basal media such as 1HCellGro/GT-T502 was used, a high NK cell content rate was similarly obtained.

As described above, according to the present invention, it was made clear that, a cell population containing a high proportion of a NK cell was effectively obtained even when a medium was changed during culture.

Example 9

Culture of NK Cell Using Gas Permeable Culture Bag (1) Preparation of Anti-Human CD3 Antibody and RetroNectin-immobilized CultiLife (Registered Trademark) 215.

A gas permeable culture bag CultiLife 215 (manufactured by TAKARA BIO INC.) was sealed so that a culture area was 86 cm$^2$. To the bag was added 10.4 mL of an ACD-A liquid containing a final concentration of 5 μg/mL of an anti-human CD3 antibody and RetroNectin, and incubated at 37° C. for 5 hours in the presence of 5% CO$_2$. The anti-CD3 antibody/RetroNectin-immobilized CultiLife 215 was washed three times with 1% HSA/physiological saline immediately before use.

(2) Separation of PBMC from Fresh Blood

Heparinized blood collection as a 30 mL portion was performed on a human healthy donor from whom informed consent had been obtained. The resulting blood was centrifuged at 700×g and room temperature for 20 minutes and then separated into a plasma fraction which was the supernatant after centrifugation and a cell fraction comprising PBMC.

The plasma fraction was subjected to inactivation treatment at 56° C. for 30 minutes, and centrifuged at 900×g and 4° C. for 30 minutes. The supernatant thereof was used in a later step, as an inactivated autologous plasma (hereinafter, referred to as plasma).

The cell fraction containing PBMC was filled up into 20 mL and diluted using 1% HSA/physiological saline. The resulting diluted cell liquid was layered on 20 mL of Ficoll-Paque PREMIUM, and centrifuged at 700×g and room temperature for 20 minutes. After centrifugation, the PBMC layer of separated layers was recovered with a pipette, filled up into 20 mL using 1% HSA/physiological saline, and centrifuged at 650×g and 4° C. for 10 minutes to remove the supernatant. Similarly, centrifugation operations were sequentially performed while centrifugation G was fallen stepwisely to 600×g and 500×g. Washing was repeated a total of three times, and the resulting PBMC was suspended in 1HGT-T551. The number of live cells and a survival rate were calculated by a trypan blue staining method, and the PBMC was subjected to each experiment.

(3) Expansion Culture of Anti-CD3 Antibody/RetroNectin-Stimulated T Cell

Into 120 mL of 1HGT-T551 was suspended $1.2 \times 10^7$ cells of the PBMC separated in Example 9-(2), and the suspension was added to the anti-CD3 antibody and RetroNectin-immobilized CultiLife 215 prepared in Example 9-(1). IL-2 was added in a final concentration of 200 U/mL, and culture was initiated at 37° C. in the presence of 5% $CO_2$ (culturing 0th day). On fourth day after culture initiation, a cell liquid in each CultiLife 215 was suspended, and 40 mL of the suspension was transferred to a gas permeable culture bag CultiLife (registered trademark) Eva (manufactured by TAKARA BIO INC.) on which nothing had been immobilized and which had been sealed so that a culture area was 430 cm². At this time, 292.6 mL of 1HGT-T551 was added so that the total liquid amount contained in CultiLife Eva became 336 mL, IL-2 was added in a final concentration of 200 U/mL and, thereafter, this was cultured at 37° C. in 5% $CO_2$. Culture was continued until seventh day. On seventh day, a necessary amount of cultured RN-T was taken out (this was used in a later step, as an AIC material) and, thereafter, plasma-free GT-T 551 in an equivalent amount to that of a cell liquid which had been left in the bag was added, and IL-2 was added in a final concentration of 200 U/mL. On eleventh day, a cell liquid in CultiLife Eva was 2-fold diluted using plasma-free GT-T551 and, thereafter, IL-2 was added in a final concentration of 200 U/mL. On fourteenth day, a necessary amount of RN-T was fractionated, and used in a later step as an AIC material.

(4) Preparation of AIC Using RN-T

Using the RN-T prepared in Example 9-(3), AIC was prepared in the same manner as that of Example 5-(3). The RN-T AIC prepared using RN-T on seventh day after culture initiation was suspended in CellGro containing 0.8% plasma, (hereinafter, referred to as 0.8% plasma/CellGro) at $2 \times 10^6$ cells/mL. The RN-T AIC prepared using RN-T on fourteenth day after culture initiation was suspended in 0.8% plasma/CellGro at $4 \times 10^6$ cells/mL.

(5) Expansion Culture of NK Cell Population

To a gas permeable culture bag CultiLife (registered trademark) Spin (manufactured by TAKARA BIO INC.) were added each $3 \times 10^7$ cells of the PBMC prepared in Example 9-(2) and the RN-T AIC prepared in Example 9-(4) (prepared using RN-T on seventh day after culture initiation). IL-2 was added in a final concentration of 200 U/mL, and OK-432 was added in a final concentration of 0.05 KE/mL. The total liquid amount was finally adjusted to 30 mL using 0.8% plasma/CellGro. Culture of the culture bag to which the cell liquids had been added was initiated at 37° C. in the presence of 5% $CO_2$ (culture 0th day). On second day after culture initiation, 30 mL of 0.8% plasma/CellGro was added to the culture bag, and IL-2 was added in a final concentration of 200 U/mL. On fourth day, IL-2 was added to the culture bag in a final concentration of 200 U/mL. On seventh day, after the total cell number in the culture bag was calculated by a trypan blue staining method, 30 mL of a cell liquid was transferred to CultiLife 215, and the RT-T AIC prepared in Example 9-(4) (prepared using RT-T on fourteenth day after culture initiation) was added so that a cell number ratio became 1:1. After IL-2 was added to this culture bag in a final concentration of 200 U/mL, the total liquid amount was adjusted to 180 mL using 0.8% plasma/CellGro. On eleventh day, 90 mL of the cell liquid in CultiLife 215 was transferred to CultiLife Eva, and 5-fold diluted using GT-T503 containing 0.8% plasma and 0.2% HSA (hereinafter, referred to as 0.8% plasma/0.2% HSA/GT-T503) to adjust the total liquid amount to 450 mL. Thereafter, IL-2 was added in a final concentration of 200 U/mL. On thirteenth day, 225 mL of the cell liquid in CultiLife Eva was 3-fold diluted using GT-T503 comprising 0.26% plasma and 0.2% HSA (hereinafter, referred to as 0.26% plasma/0.2% HSA/GT-T503) to adjust the total liquid amount to 675 mL. Thereafter, IL-2 was added in a final concentration of 200 U/mL and, thereafter, this was transferred to CultiLife Eva. Culture was continued until sixteenth day. On thirteenth and sixteenth days after culture initiation, regarding each sampled cell, the number of live cells was measured by a trypan blue staining method, and the number was compared with the cell number at culture initiation to calculate an expansion culturing rate. Results are shown in Table 16.

TABLE 16

| Expansion culturing rate | |
|---|---|
| 13th day after culture initiation | 16th day after culture initiation |
| ×43.1 | ×258.7 |

As shown in Table 16, it was made clear that even when culture was performed using a gas permeable culture bag, a high expansion culturing rate was obtained.

(6) Analysis of CD3-Positive CD56-Negative Cell (T Cell), CD3-Negative CD56-Positive Cell (NK Cell) and CD16-Positive CD56-Positive Cell Content Rates Regarding the cells on sixteenth day after culture initiation prepared in Example 9-(5), a NK cell content rate was analyzed in the same manner as that of Example 1-(4) except that a PC5-labeled mouse anti-human CD16 antibody (manufactured by Beckman Coulter Inc.) was used in combination, and CD3-positive CD56-negative cell (T cell) and CD16-positive CD56-positive cell content rates were also analyzed. Results are shown in Table 17.

TABLE 17

| Cell content rate (%) | | |
|---|---|---|
| $CD3^+$ $CD56^-$ | $CD3^-$ $CD56^+$ | $CD16^+$ $CD56^+$ |
| 1.73 | 92.76 | 97.52 |

As shown in Table 17, even when culture using OK-432 and RN-T AIC was performed using a gas permeable culture bag, a high NK cell content rate was obtained. And, it was confirmed that the NK cell obtained after culture expressed CD16 at a high rate, and therefore, contained a high proportion of a highly functional NK cell expressing a CD16 molecule which played an important role in exerting antibody-dependent cell-mediated cytotoxicity. In the resulting cell population, only a very small number of a T cell was recognized.

(7) Measurement of Cytotoxic Activity

Regarding the cells on sixteenth day after culture initiation prepared in Example 9-(5), cytotoxic activity was measured in the same manner as that of Example 1-(5) except that K562, Daudi, an esophageal squamous epithelial cancer cell strain T. Tn, a mammary gland cancer-derived cell strain MCF7, a lung cancer cell strain A549, a melanoma cell strain A375, a stomach cancer cell strain MKN45 and a colon cancer cell strain HT29 shown in the following Table were used as target cells, and measurement was performed at an E/T ratio of 30, 10, 3 or 1. Results of measurement of cytotoxic activity are shown in Table 18.

TABLE 18

| E/T ratio | Cytotoxic activity (%) | | | | | | | |
|---|---|---|---|---|---|---|---|---|
| | K562 | Daudi | T.Tn | MCF7 | A549 | A375 | MKN45 | HT29 |
| 30 | 74.96 | 81.16 | 20.72 | 46.83 | 73.64 | 61.08 | 12.02 | 30.24 |
| 10 | 69.03 | 80.02 | 10.54 | 39.87 | 61.81 | 52.54 | 13.87 | 22.59 |
| 3 | 69.62 | 76.70 | 9.27 | 27.32 | 38.07 | 32.09 | 0 | 12.19 |
| 1 | 60.39 | 73.71 | 0 | 13.14 | 17.82 | 14.74 | 2.48 | 3.83 |

As shown in Table 18, it was made clear that a cell population obtained by culture using OK-432, RN-T AIC and a gas permeable culture bag exhibited high cytotoxic activity on various target cells. The activity was confirmed on not only K562 known as a NK cell-sensitive cell strain, and Daudi known as an MHC class I-non-expressing cell strain, but also various MHC class I-expressing cell strains. It was confirmed that the cell population was a highly functional NK cell which exerted cytotoxic activity on a variety of cancer cell strains.

That is, according to the present invention, a cell population exhibiting a CD3-negative CD56-positive CD16-positive phenotype and having high cytotoxicity can be obtained at a high purity.

Example 10

Culture of NK Cell Using OK-432 and AIC (Comparison with Allogeneic-Irradiated Cell)

(1) Preparation of Anti-Human CD3 Antibody and RetroNectin-Immobilized Plate

In the same manner as that of Example 3-(1), an anti-human CD3 antibody and RetroNectin-immobilized plate was prepared.

(2) Expansion Culture of Anti-CD3 Antibody/RetroNectin-Stimulated T Cell

Expansion culture of RN-T was performed in the same manner as that of Example 6-(2) except that a RN-T was cultured from PBMC derived from the same donor as a donor who provided PBMC as a material upon culture of a NK cell (hereinafter, referred to as autologous RN-T), and a RN-T was cultured from PBMC derived from a different donor (hereinafter, referred to as allo RN-T).

(3) Preparation of X-ray-irradiated Cell Using RN-T

Using the autologous RN-T and the allo RN-T prepared in Example 10-(2), and X-ray-irradiated cells were prepared in the same manner as that of Example 5-(3).

(4) Expansion Culture of NK Cell Population

Expansion culture of a NK cell was performed in the same manner as that of Example 1-(3) except that 5HCellGro was used as a culture medium and the autologous RN-T X-ray-irradiated cell (having the same meaning as that of RN-T AIC) and the allo RN-T X-ray-irradiate cell prepared in Example 10-(3) were used as AIC.

On second day after culture initiation, each 1 mL of 5HCellGro was added to each well, and IL-2 was added in a final concentration of 200 U/mL. On fourth day, IL-2 was added to an each well in a final concentration of 200 U/mL. On seventh day, a cell liquid of each well was 3-fold diluted using 5HCellGro, and 2 mL of the cell liquid was transferred to a new 24-well cell culture plate. On ninth day, the cell liquid of each well was similarly 3-fold diluted, and 2 mL of the diluted cell liquid was transferred to a new 24-well cell culture plate. Further, on eleventh day, the cell liquid of each well was similarly 2.5-fold diluted, and 4 mL of the diluted cell liquid was transferred to a new 12-well cell culture plate. On every subculturing day, IL-2 was added in a final concentration of 200 U/mL. Culture of these cells was continued until fifteenth day. Regarding cells sampled on eleventh and fifteenth days after culture initiation, the number of live cells was measured by a trypan blue staining method, and the number was compared with the cell number at culture initiation to calculate an expansion culturing rate. Results are shown in Table 19.

TABLE 19

| | | Expansion culturing rate | |
|---|---|---|---|
| X-ray-irradiated cell (RN-T AIC) | OK-432 | $11^{th}$ day after culture initiation | $15^{th}$ day after culture initiation |
| Autologous RN-T X-ray-irradiated cell | + | ×13.05 | ×86.48 |
| Allo RN-T X-ray-irradiated cell | + | ×15.30 | ×85.64 |

As shown in Table 19, whether the used RN-T was autologous or allo, an equivalent expansion culturing rate was obtained.

It is generally known that, when two kinds of lymphocyte cells from different donors are mixed, a lymphocyte recognizes a allo antigen and is proliferated due to an allogeneic mixed lymphocyte reaction (hereinafter, referred to as Allo-MLR) which does not occur when autologous cells are mixed, and therefore, a X-ray-irradiated allo cell is widely generally used as a feeder cell. However, it is surprising that even when RN-T AIC which was an X-ray-irradiated autologous cell was used in place of an X-ray-irradiated allo cell in culture of a NK cell, the similar NK cell expansion culturing effect was obtained. Further, use of autologous-derived RN-T AIC in NK culture results in remarkable improvement in the safety from a view point of safety of medical care where a NK cell after culture is administered to the donor.

(5) Analysis of CD3-negative CD56-positive Cell (NK Cell) and CD16-Positive CD56-Positive Cell Content Rates Regarding the cells on fifteenth day after culture initiation prepared in Example 10-(4), a NK cell content rate and a CD16-positive CD56-positive cell content rate were analyzed in the same manner as that of Example 9-(6). Results are shown in Table 20.

TABLE 20

| X-ray-irradiated cell (RN-T AIC) | OK-432 | Cell content rate (%) | |
|---|---|---|---|
| | | CD3⁻CD56⁺ | CD16⁺CD56⁺ |
| Autologous RN-T X-ray-irradiated cell | + | 94.30 | 84.90 |
| Allo RN-T X-ray-irradiated cell | + | 87.49 | 79.04 |

As shown in Table 20, when autologous RN-T AIC was used, a higher NK cell content rate and a higher CD16-positive NK cell content rate were obtained as compared with an allo RN-T X-ray-irradiated cell-addition group.

That is, it was made clear that a process of culturing a NK cell in the presence of a combination of OK-432 and antologous RN-T AIC provided NK cells having a higher NK cell content rate and a higher CD16-positive NK cell rate, and having high safety.

Example 11

Culture of NK Cell Using OK-432 and AIC
(Differentiation Stage of Cultured NK Cell)

(1) Preparation of X-ray-irradiated Cell Using PBMC

Using the PBMC prepared in Example 1-(1), PBMC AIC was prepared in the same manner as that of Example 3-(3). The prepared PBMC AIC was suspended in 5HCellGro, and used in the following experiment.

(2) Expansion Culture of NK Cell Population Expansion culture of a NK cell was performed in the same manner as that of Example 1-(3) except that 5HCellGro was used as a culture medium and PBMC AIC prepared in Example 11-(1) was used as AIC.

On seventh day after culture initiation, a cell liquid of each well was 8-fold diluted using 5HCellGro, and 2 mL of the cell liquid was transferred to a new 24-well cell culture plate. At this time, 1×10$^6$ cells of the PBMC AIC prepared in Example 11-(1) was added to each well, and IL-2 was added in a final concentration of 200 U/mL. The same subculturing operation was performed on tenth day and fifteenth day. The dilution rates of the cell liquids on tenth day and fifteenth day were 6-fold and 3-fold, respectively. Further, on eighteenth day, the cell liquid of each well was similarly 4-fold diluted, and 4 mL of the diluted cell liquid was transferred to a new 12-well cell culture plate. On every subculturing day, IL-2 was added in a final concentration of 200 U/mL. Culture of these cells was continued until twenty-second day after culture initiation. Regarding a part of the culture, the number of live cells was measured by a trypan blue staining method, and the number was compared with the cell number at culture initiation to calculate an expansion culturing rate. Results (expansion culturing rate) are shown in Table 21.

TABLE 21

| 22$^{nd}$ day after culture initiation |
|---|
| ×334.08 |

(3) Analysis of CD3-negative CD56-positive Cell (NK Cell), CD16-positive CD56-positive Cell, CD34-negative CD117-negative Cell, and CD94-positive CD56-Positive Content Rates Regarding the cells on twenty-second day after culture initiation prepared in Example 11-(2), a NK cell content rate and a CD16-positive CD56-positive cell ratio were analyzed in the same manner as that of Example 9-(6) except that CD34-positive CD117-positive cell and CD94-positive CD56-positive content rates were similarly analyzed using a FITC-labeled mouse anti-human CD34 antibody (manufactured by Becton, Dickinson and Company), a PE-labeled mouse anti-human CD117 antibody (manufactured by R&D Systems, Inc.) and a FITC-labeled mouse anti-human CD94 antibody (manufactured by eBioscience, Inc.). Results are shown in Table 22.

TABLE 22

| Cell content rate (%) | | | |
|---|---|---|---|
| CD3⁻CD56⁺ | CD16⁺CD56⁺ | CD34⁺CD117⁺ | CD94⁺CD56⁺ |
| 84.52 | 84.03 | 0.18 | 79.6 |

As shown in Table 22, in a cell population obtained by a method using a combination of OK-432 and PBMC AIC, a CD56-positive, CD16-positive, CD34-negative, CD117-negative and CD94-positive cell accounted for a majority.

It is known that a NK cell is classified into four differentiation stages depending on expression of its surface antigen. Among them, particularly, a CD56-positive, CD16-positive, CD34-negative, CD117-negative and CD94-positive cell is a phenotype seen at the final differentiation stage, and is known to be a matured NK cell exerting high cytotoxic activity.

That is, it was made clear that a matured NK cell was effectively obtained by the present invention, and an effective process for preparing a mature NK cell was provided by the present invention.

Example 12

Culture of NK Cell Using OK-432 and AIC
(Comparison of OK-432 and AIC Effectivenesses)

(1) Preparation of Anti-Human CD3 Antibody and RetroNectin-immobilized Plate

In the same manner as that of Example 3-(1), an anti-human CD3 antibody and RetroNectin-immobilized plate was prepared.

(2) Expansion Culture of Anti-CD3 Antibody/RetroNectin-stimulated T Cell

Expansion culture of RN-T was performed in the same manner as that of Example 6-(2) except that plasma-free GT-T551 was used on seventh day after culture initiation and thereafter.

(3) Preparation of AIC Using RN-T

Using the RN-T prepared in Example 12-(2), RN-T AIC was prepared in the same manner as that of Example 5-(3) except that RN-T on seventh day after culture initiation was suspended in CellGro containing 0.8% human type AB serum (hereinafter, referred to as 0.8HCellGro), and RN-T on fourteenth day was suspended in GT-T502 containing 0.8% human type AB serum (hereinafter, referred to as 0.8HGT-T502) and, thereafter, the suspensions were used in the following experiment.

(4) Expansion Culture of NK Cell Population

Expansion culture of a NK cell was performed in the same manner as that of Example 1-(3) except that a OK-432- or RN-T AIC-non-addition group was also set. As a basal culture medium, 0.8HCellGro was used from culture initiation to fourth day, 0.8HGT-T502 was used on seventh day, and GT-T502 comprising 0.29% human type AB serum (hereinafter, referred to as 0.29HGT-T502) was used on thirteenth day. On first day after culture initiation, 1 mL of 0.8HCellGro was added to each well, and IL-2 was added to each well in a final concentration of 200 U/mL. On fourth day, IL-2 was added to each well in a final concentration of 200 U/mL. On seventh day, a cell liquid of each well was 6-fold diluted using 0.8HGT-T502, and 2 mL of the cell liquid was transferred to a new 24-well cell culture plate. The same subculturing operation was performed on eleventh day and thirteenth day, and culture was continued until seventeenth day. The dilutions of the cell liquids on tenth day and fifteenth day were 5-fold dilution with 0.8HGT-T502, and 3-fold dilution with 0.29HGT-T502, respectively. On seventh day after culture initiation, regarding a part of conditions, each $1 \times 10^6$ cells/well of the RN-T AIC prepared in Example 12-(3) was added.

On eleventh day, thirteenth day and seventeenth day after culture initiation, the number of live cells was measured by a trypan blue staining method, and the number was compared with the cell number at culture initiation to calculate an expansion culturing rate. Results are shown in Table 23.

TABLE 23

| | Stimulation with AIC | | Expansion culturing rate | | |
|---|---|---|---|---|---|
| OK-432 | $0^{th}$ day after culture initiation | $7^{th}$ day after culture initiation | $11^{th}$ day after culture initiation | $13^{th}$ day after culture initiation | $17^{th}$ day after culture initiation |
| + | + | + | ×23.62 | ×48.03 | ×310.46 |
| + | + | − | ×22.99 | ×47.13 | ×256.65 |
| + | − | − | ×2.43 | ×13.21 | ×129.45 |
| − | + | − | ×18.52 | ×45.03 | ×182.36 |
| − | − | − | ×3.87 | ×33.92 | ×174.93 |

As shown in Table 23, a higher expansion culturing rate was obtained on eleventh, thirteenth and seventeenth days by combining OK-432 and RN-T AIC, as compared with an OK-432-non-addition group, an AIC-non-addition group, and an OK-432 and AIC-non-addition group.

(5) Analysis of CD3-negative CD56-positive Cell (NK Cell) Content Rate, CD3-Positive CD56-Negative Cell (T Cell) Content Rate, and CD16-Positive CD56-Positive Cell (NK Cell) Content Rate Regarding the cells on seventeenth day after culture initiation prepared in Example 12-(4), a NK cell content rate, a CD3-positive CD56-negative cell rate, and a CD16-positive CD-56-positive cell were analyzed in the same manner as that of Example 9-(6). Results are shown in Table 24.

TABLE 24

| | Stimulation with AIC | | Cell content rate (%) | | |
|---|---|---|---|---|---|
| OK-432 | $0^{th}$ day after culture initiation | $7^{th}$ day after culture initiation | CD3$^+$ CD56$^-$ | CD3$^-$ CD56$^+$ | CD16$^+$ CD56$^+$ |
| + | + | + | 0.91 | 97.18 | 97.51 |
| + | + | − | 0.23 | 98.21 | 98.09 |
| + | − | − | 84.64 | 6.20 | 8.19 |
| − | + | − | 22.51 | 48.25 | 87.33 |
| − | − | − | 63.16 | 18.32 | 31.42 |

As shown in Table 24, a higher NK cell content rate was obtained by combining OK-432 and RN-T AIC, as compared with an OK-432-non-addition group, an AIC-non-addition group, and an OK-432 and AIC-non-addition group. In addition, a NK cell content rate was low in an OK-432-non-addition group, an AIC-non-addition group, and an OK-432 and AIC-non-addition group. Particularly, a CD3-positive CD56-negative cell, that is, T cell was predominantly proliferating in an AIC-non-addition group, and an OK-432 and AIC-non-addition group. Contrary to these groups, in groups using a combination of OK-432 and RN-T AIC, a NK cell was proliferating at an extremely high rate, and the resulting NK cell was highly expressing CD16 which was an important molecule for exerting antibody-dependent cell-mediated cytotoxicity. That is, it was made clear that a NK cell having a high NK content rate and a high CD16-positive rate was obtained by combining OK-432 and AIC.

(6) Analysis of NK Cell Expansion Culturing Rate

Regarding PBMC before culture initiation and the cells on seventeenth day after culture initiation prepared in Example 12-(4), a NK cell content rate was analyzed, in the same manner as that of Example 9-(6). Using the expansion culturing rate obtained in Example 12-(4) (in terms of a total cell), the total cell was compared with the NK cell number at culture initiation to calculate a NK cell expansion culturing rate on seventeenth day after culture initiation (see the following equation (2)). Results are shown in Table 25.

[Mathematic 2]

$$\text{NK cell expansion culturing rate(-fold)} = \{\text{expansion culturing rate(in terms of total cell)}\} \times \{(\text{NK cell content rate on seventeenth day after culture initiation})/(\text{NK cell content rate at culture initiation})\} \quad \text{Equation (2)}$$

TABLE 25

| | Stimulation with AIC | | | NK cell content rate (%) | | |
|---|---|---|---|---|---|---|
| OK-432 | $0^{th}$ day after culture initiation | $7^{th}$ day after culture initiation | Expansion culturing rate (Total cell number) | $0^{th}$ day after culture initiation | $17^{th}$ day after culture initiation | NK cell expansion culturing rate |
| + | + | + | ×310.46 | 9.8 | 97.18 | ×3078.74 |
| + | + | − | ×256.65 | | 95.21 | ×2572.33 |
| + | − | − | ×129.45 | | 6.2 | ×85.72 |
| − | + | − | ×182.36 | | 48.25 | ×899.80 |
| − | − | − | ×174.93 | | 18.32 | ×342.28 |

As shown in Table 25, it was made clear that a higher NK cell expansion culturing rate is obtained by combining OK-432 and RN-T AIC, as compared with an OK-432-non-addition group, an AIC-non-addition group, and an OK-432 and AIC-non-addition group.

Example 13

Analysis of Surface Antigen of NK Cell Population After Expansion Culturing (1) Expansion Culture of NK Cell Population Expansion culture of a NK cell was performed in the same manner as that of Example 9-(5) except that on thirteenth day after culture initiation, 225 mL of a cell liquid in CultiLife Eva was 3-fold diluted using GT-T503 comprising 0.29% plasma and 0.2% HSA (hereinafter, referred to as 0.29% plasma/0.2% HSA/GT-T503), so that the total liquid amount was 675 mL, thereafter, IL-2 was added in a final concentration of 200 U/mL, and the cell liquid was transferred to CultiLife Eva. On fifteenth day after culture initiation, IL-2 was added to a culture bag in a final concentration of 200 U/mL. On culturing eighteenth day, 338 mL of the cell liquid in CultiLife Eva was adjusted to a total liquid amount of 675 mL using 0.29% plasma/0.2% HSA/GT-T503, thereafter, IL-2 was added in a final concentration of 200 U/mL, and the cell liquid was transferred to CultiLife Eva. Culture was continued until twentieth day. Regarding cells sampled on eighteenth and twentieth days after culture initiation, the number of live cells was measured by a trypan blue staining method, and the number was compared with the cell number at culture initiation to calculate an expansion culturing rate. Results are shown in Table 26.

TABLE 26

| Expansion culturing rate | |
|---|---|
| 18th day after culture initiation | 20th day after culture initiation |
| ×560.7 | ×985.5 |

(2) Analysis of Surface Antigen of NK Cell After Culturing

Regarding the cells on twentieth day after culture initiation prepared in Example 13-(1), a T cell content rate, a NK cell content rate and a CD16-positive CD56-positive cell content rate were analyzed in the same manner as that of Example 9-(6) except that NKp44-positive CD56-positive cell, NKp46-positive CD56-positive cell, CD25-positive CD56-positive cell and CD62L-positive CD56-positive cell content rates were also analyzed using a FITC-labeled mouse anti-human NKp44 antibody (manufactured by SANTA CRUZ BIOTECHNOLOGY, Inc.), a FITC-labeled mouse anti-human NKp46 antibody (manufactured by R&D Systems, Inc.), a FITC-labeled mouse anti-human CD25 antibody (manufactured by DakoCytomation Co., Ltd.), and a PC5-labeled mouse anti-human CD62L antibody (manufactured by Beckman Coulter Inc.). Results are shown in Table 27.

TABLE 27

| Cell content rate (%) | | | | | | |
|---|---|---|---|---|---|---|
| $CD3^+$ $CD56^+$ | $CD3^-$ $CD56^+$ | $CD16^+$ $CD56^+$ | $NKp44^+$ $CD56^+$ | $NKp46^+$ $CD56^+$ | $CD25^+$ $CD56^+$ | $CD62L^+$ $CD56^+$ |
| 2.86 | 97.00 | 98.78 | 26.13 | 75.74 | 11.87 | 81.42 |

As shown in Table 27, cell populations obtained by a process using a combination of OK-432 and RN-T AIC were expressing CD56, CD16, NKp44, NKp46, CD25, and CD62L.

NKp44 and NKp46 belong to a natural cytotoxicity receptor (NCR) family, and are said to be involved in cytotoxic activity by NK cells. NKp44 is not expressed on NK cells at a stationary stage, and is expressed only on activated NK cells. NKp46 is a surface antigen common to NK cells, which is expressed only on NK cells. CD25 is stimulated with IL-2, and is expressed on activated NK cells. CD62L plays an important role upon homing of lymphocytes, and is known to be involved in accumulation into an inflammatory site from a blood stream.

That is, it was made clear that a matured and activated NK cell was effectively obtained according to the process of the present invention, and an effective process for preparing a mature NK cell was provided according to the present invention.

Example 14

Culture of NK Cell Using a Gas Permeable Culture Bag (1) Expansion Culture of Anti-CD3 Antibody/RetroNectin-stimulated T Cell Into 120 mL of 1HGT-T551 was suspended $1.2 \times 10^7$ cells of PBMC separated in the same manner as that of Example 9-(2), the suspension was added to anti-CD3 antibody and RetroNectin-immobilized CultiLife 215 prepared in the same manner as that of Example 9-(1), IL-2 was added in a final concentration of 200 U/mL, and culture was initiated at 37° C. in the presence of 5% $CO_2$ (culture $0^{th}$ day). On fourth day after culture initiation, a cell liquid in CultiLife 215 was suspended, and 30 mL of the suspension was transferred to a gas permeable culture bag CultiLife Eva on which nothing had been immobilized and which had been sealed so that a culture area became 320 $cm^2$. At this time, 220 mL of 1HGT-T551 was added so that the total liquid amount in CultiLife Eva became 250 mL, IL-2 was added in a final concentration of 200 U/mL and, thereafter, this was cultured at 37° C. in 5% $CO_2$. Culture was continued until seventh day. On seventh day, a necessary amount of cultured RN-T was taken out (which was used in a later step as an AIC material). Thereafter, plasma-free GT-T551 in an equivalent amount to that of the cell liquid left in the bag, and IL-2 in a final concentration of 200 U/mL were added to the bag. On eleventh day, the cell liquid in CultiLife Eva was 2-fold diluted using plasma-free GT-T551 and, thereafter, IL-2 was added in a final concentration of 200 U/mL. On fourteenth day, a necessary amount of RN-T was taken out, and then was used as an AIC material in a later step.

(2) Preparation of AIC Using RN-T

Using the RN-T prepared in Example 14-(1), AIC was prepared in the same manner as that of Example 5-(3). The RN-T AIC prepared using RN-T on seventh day after culture initiation was suspended in 0.8% plasma/CellGro at $2 \times 10^6$ cells/mL, and the RN-T AIC prepared using RN-T on fourteenth day after culture initiation was suspended in 0.8% plasma/CellGro at $4 \times 10^6$ cells/mL.

(3) Expansion Culture of NK Cell Population

Expansion culture of a NK cell population was performed in the same manner as that of Example 9-(5) except that CultiLife 215 was used at culture initiation, and a dilution operation was performed on fourteenth day in place of thirteenth day. Culture was continued until eighteenth day. Regarding cells sampled on eighteenth day after culture initiation, the number of live cells was measured by a trypan blue staining method, and the number was compared with the cell number at culture initiation to calculate an expansion culturing rate. Results are shown in Table 28.

TABLE 28

| Expansion culturing rate 18th day after culture initiation |
|---|
| ×393.8 |

As shown in Table 28, it was made clear that even when a gas permeable culture bag CultiLife 215 was used at culture initiation, a high expansion culturing rate was obtained. That is, it was made clear that, regardless of the kind of a gas permeable culture bag at culture initiation, the desired effect was exerted.

(4) Analysis of CD3-positive CD56-negative Cell (T Cell), CD3-negative CD56-positive Cell (NK Cell) and CD16-positive CD56-positive Cell Content Rates Regarding the cells on eighteenth day after culture initiation prepared in Example 14-(3), a T cell content rate, a NK cell content rate and a CD16-positive CD56-positive cell content rate were analyzed in the same manner as that of Example 9-(6) except that a CD56-positive NKG2D-positive cell content rate was also analyzed using a PE-labeled mouse anti-human NKG2D antibody (manufactured by Beckman Coulter Inc.). Results are shown in Table 29.

TABLE 29

| Cell content rate (%) | | | |
|---|---|---|---|
| $CD3^+$ $CD56^-$ | $CD3^-$ $CD56^+$ | $CD16^+$ $CD56^+$ | $NKG2D^+$ $CD56^+$ |
| 0.35 | 99.23 | 98.59 | 98.08 |

As shown in Table 29, even when culture using OK-432 and RN-T AIC was performed using a gas permeable culture bag CultiLife 215 at culture initiation, a high NK cell content rate was obtained. It was confirmed that NK cells obtained after culture expressed CD16 and NKG2D at a high rate, and contained a high proportion of a highly functional NK cell expressing a CD16 molecule which played an important role in exerting antibody-dependent cell-mediated cytotoxicity and a highly functional NK cell exhibiting high cytotoxic activity through NKG2D.

(5) Measurement of Cytotoxic Activity

Regarding the cells on eighteenth day after culture initiation prepared in Example 14-(3), cytotoxic activity was measured in the same manner as that of Example 1-(5) except that K562 and A549 were used as target cells, and measurement was performed at an E/T ratio of 10, 3, 1 and 0.3. Results of measurement of cytotoxic activity are shown in Table 30.

TABLE 30

| | Cytotoxic activity (%) | |
|---|---|---|
| E/T ratio | K562 | A549 |
| 10 | 84.39 | 77.32 |
| 3 | 81.91 | 60.85 |
| 1 | 74.47 | 32.68 |
| 0.3 | 37.77 | 17.88 |

As shown in Table 30, it was made clear that cell populations obtained by culture using OK-432, RN-T AIC and a gas permeable culture bag CultiLife 215 at culture initiation exhibited high cytotoxic activity on various target cells. The activity thereof was confirmed on not only K562 known as a NK cell-sensitive cell strain, but also an MHC class I-expressing cell strain A549. It was confirmed that these cell populations were a highly functional NK cell exerting cytotoxic activity on a variety of cancer cell strains.

That is, according to the present invention, a cell population exhibiting a CD3-negative CD56-positive CD16-positive phenotype and having high cytotoxicity can be obtained at a high purity.

Example 15

Culture of NK Cell Using OK-432 and AIC
(Comparison of Cytotoxic Activity)

(1) Preparation of AIC Using PBMC

PBMC AIC was prepared in the same manner as that of Example 1-(2) except that the prepared PBMC AIC was suspended in 0.8HCellGro at $2\times10^6$ cells/mL, and used in the following experiment.

(2) Expansion Culture of NK Cell Population

Expansion culture of a NK cell was performed in the same manner as that of Example 1-(3) except that 0.8HCellGro was used as a culture medium and PBMC AIC prepared in Example 15-(1) was used as AIC.

On first day after culture initiation, each 1 mL of 0.8HCellGro was added to each well, and IL-2 was added in a final concentration of 200 U/mL. On third day, IL-2 was added to each well in a final concentration of 200 U/mL. On seventh day, a cell liquid of each well was 6-fold diluted using 0.8HCellGro, and 1.674 mL of the diluted cell liquid was transferred to a new 24-well cell culture plate. On tenth day, the cell liquid of each well was 5-fold diluted using 0.8HGT-T502, and 2 mL of the diluted cell liquid was transferred to a new 24-well cell culture plate. On every subculturing day, IL-2 was added to each well in a final concentration of 200 U/mL. Cells on fourteenth day after culture initiation was adjusted to $1\times10^6$ cells/mL using 5HRPMI, interferon (IFN) alpha (product name Sumiferon: Dainippon Sumitomo Pharma Co., Ltd.; hereinafter, referred to as IFN-α) was added thereto in a final concentration of 1000 U/mL, and allowed to stand in a 5% $CO_2$ incubator at 37° C. for 1 hour. After this cell liquid was washed, it was suspended in 5HRPMI (IFNα treatment). At this time, an IFN-α non-addition group (IFNα-untreated) was also made.

(3) Measurement of Cytotoxic Activity

Regarding the cells on fourteenth day after culture initiation prepared in Example 15-(2), cytotoxic activity was measured in the same manner as that of Example 1-(5) except that K562, A549 and HT29 were used as target cells, and measurement was performed at an E/T ratio of 10, 3, 1 and 0.3. Results of measurement of cytotoxic activity are shown in Table 31.

TABLE 31

| | | Cytotoxic activity (%) | |
|---|---|---|---|
| Target cell | E/T ratio | IFNα-untreated | IFNα-treated |
| K562 | 10 | 74.22 | 77.37 |
| | 3 | 71.00 | 71.30 |
| | 1 | 49.97 | 52.76 |
| | 0.3 | 19.43 | 23.03 |
| A549 | 10 | 51.68 | 72.28 |
| | 3 | 21.48 | 52.70 |
| | 1 | 5.57 | 27.51 |
| | 0.3 | −1.22 | 11.07 |
| HT-29 | 10 | 33.72 | 46.90 |
| | 3 | 16.84 | 32.69 |
| | 1 | 5.44 | 18.81 |
| | 0.3 | −3.18 | 8.67 |

As shown in Table 31, it was made clear that cytotoxic activity on various target cells was enhanced by treating a cell population obtained by culture using OK-432 and RN-T AIC with IFN-α. Also, it was confirmed that this cell population is a highly functional NK cell exerting activity on not only K562 known as a NK cell-sensitive cell strain, but also a variety of cancer cell strains.

Example 16

Culture of NK Cell Using OK-432 and Mild Heat-Treated Cell (Comparison of Mild Heat-Treated Cell Number)

(1) Preparation of Anti-Human CD3 Antibody and RetroNectin-Immobilized Plate

In the same manner as that of Example 3-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of Mild Heat-Treated Cell Using RN-T

RN-T cultured in Example 16-(2) was adjusted to $5\times10^6$ cells/mL with 5HRPMI, each 0.6 mL of the suspension was transferred to a 1.5 mL tube (manufactured by WATSON Co., Ltd., or manufactured by Treff AG), and then mild heat-treated using a water bath at 45° C. for 1 hour. After the treated cell liquid was recovered and centrifuged, the supernatant was removed, and the cell liquid was adjusted to 2, 4 or $10\times10^6$ cells/mL with 0.8HCellGro (hereinafter, the RN-T cell after mild heat treatment is referred to as mild heat-treated RN-T).

(4) Expansion Culture of NK Cell Population

Expansion culture of a NK cell was performed in the same manner as that of Example 12-(4) except that at culture initiation, each 0.95 mL/well of a Responder cell and the mild heat-treated RN-T which had been adjusted to each cell concentration in Example 16-(3) were added to a 12-well culture plate, so that the total was 1.9 mL/well. At this time, a group of mild heat-treated RN-T condition and addition of only OK-432 (hereinafter, referred to as control group) was set. The operation performed on thirteenth day in Example 12-(4) was performed on fourteenth day in the present Example, and culture was continued until eighteenth day. As a basal culture medium, 0.8HCellGro was used until seventh day after culture initiation, 0.8HGT-T502 was used on eleventh day, and 0.3HGT-T502 was used on fourteenth day. On eighteenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 32.

TABLE 32

| Mild heat-treated RN-T | | | |
|---|---|---|---|
| Cell number at culture initiation ($\times 10^6$ cells) | Ratio of Responder cell and mild heat-treated RN-T | Expansion culturing rate | NK cell content rate (%) |
| 1.9 | 1:1 | ×349.6 | 96.2 |
| 3.8 | 1:2 | ×442.5 | 97.8 |
| 9.5 | 1:5 | ×401.6 | 98.4 |
| Control group | — | ×223.9 | 88.1 |

As shown in Table 32, a higher expansion culturing rate and a higher NK cell content rate were obtained in a mild heat-treated RN-T-addition group by using OK-432 and mild heat-treated RN-T, as compared with a control group. These effects were not limited by the ratio of mild heat-treated RN-T to a Responder cell at culture initiation, and the effects were confirmed under a wide range of conditions.

That is, it was made clear that a high purity NK cell was obtained at a high expansion culturing rate by combining OK-432 and mild heat-treated RN-T in culture of a NK cell.

Example 17

Measurement of Antibody-Dependent Cell-Mediated Cytotoxicity (ADCC) of NK Cell (1) Expansion Culture of NK Cell Population Expansion culture of a NK cell was performed in the same manner as that of Example 16-(4) except that at culture initiation, each 0.95 mL/well of a Responder cell and the AIC prepared in the same manner as that of Example 5-(3) were added, so that the total was 1.9 mL/well. Culture was continued until twentieth day, a cell liquid was 2-fold diluted using GT-T502 not containing serum and, thereafter, IL-2 was added in a final concentration of 200 U/mL.

(2) Measurement of Antibody-Dependent Cell-Mediated Cytotoxicity (ADCC) of NK Cell Regarding the cells on twentieth day after culture initiation prepared in Example 17-(1), cytotoxic activity was measured in the same manner as that of Example 1-(5) except that breast cancer cell strains BT-474 and SKBR3, and a stomach cancer cell strain NCI-N87 were used, a Trastuzumab preparation (product name, for Herceptin injection: manufactured by Chugai Pharmaceutical Co., Ltd.) was added in a final concentration of 10 μL/mL to each cell strain which had been adjusted to $1\times10^6$ cells/mL using 1% BSA/DPBS, and incubated at 4° C. for 30 minutes. The cells were centrifuged, washed, and adjusted to $2\times10^6$ cells/mL with a RPMI1640 medium containing 5% bovine fetal serum and the resulting cell liquid was used as a target cell. At this time, the E/T ratio was 10, 3 or 1, and a group with no Trastuzumab preparation added thereto was also made. Results of measurement of cytotoxic activity are shown in Table 33.

TABLE 33

| | E/T | Cytotoxic activity (%) | |
|---|---|---|---|
| Target cell | ratio | Trastuzumab-untreated | Trastuzumab-treated |
| BT-474 | 10 | 16.61 | 66.87 |
| | 3 | 12.79 | 60.33 |
| | 1 | 7.49 | 44.63 |
| SKBR3 | 10 | 16.61 | 64.27 |
| | 3 | 13.87 | 41.09 |
| | 1 | 10.38 | 34.48 |
| NCI-N87 | 10 | 32.99 | 78.27 |
| | 3 | 21.37 | 57.03 |
| | 1 | 10.16 | 39.03 |

A Trastuzumab preparation is an antibody bound with Her2 (Human Epidermal Growth Factor Receptor Type2) which serves as an oncogene, and evokes antibody-dependent cell-mediated cytotoxicity (ADCC) via a Fc receptor (CD16 molecule etc.) of a NK cell. As shown in Table 33, it was made clear that a cell population obtained by culture using OK-432 and RN-T AIC exhibited further high cytotoxic activity on various target cells treated with a Trastuzumab preparation. The cell strain used in the present Example was a Her2-highly expressing strain, and it was confirmed that these cell populations are a highly functional NK cell exerting high antibody-dependent cell-mediated cytotoxicity on a variety of Her2-expressing cancer cell lines.

Example 18

Culture of NK Cell Using OK-432 and AIC (Comparison of Added AIC Amount)

(1) Preparation of Anti-Human CD3 Antibody and RetroNectin-Immobilized Plate

An anti-human CD3 antibody and RetroNectin-immobilized plate was prepared in the same manner as that of Example 3-(1) except that the anti-CD3 antibody/RetroNectin-immobilized plate was washed two times with DPBS, and once with GT-T551 immediately before use.

(2) Expansion Culture of Anti-CD3 Antibody/RetroNectin-Stimulated T Cell

In the same manner as that of Example 3-(2), expansion culture of RN-T was performed.

(3) Preparation of AIC Using RN-T

Using the RN-T prepared in Example 18-(2), AIC was prepared in the same manner as that of Example 3-(3) except that the RN-T recovered on seventh day after culture initiation was suspended in 0.8HCellGro after X-ray irradiation, and used in the following experiment.

(4) Expansion Culture of NK Cell Population

Expansion culture of a NK cell was performed in the same manner as that of Example 12-(4) except that the cell number of RN-T AIC to be added was set so as to be 1-fold, 5-fold or 10-fold relative to a Responder cell, and OK-432 was added to all groups. As a basal culture medium, 0.8HCellGro was used until eleventh day from culture initiation, and the operations on fourth, seventh and thirteenth days in Example 12-(4) were performed on fifth, eighth and fifteenth days in the present Example, respectively. On eighteenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 34.

TABLE 34

| Ratio of Responder cell and AIC | Expansion culturing rate | NK cell content rate (%) |
|---|---|---|
| 1:1 | ×260.5 | 96.5 |
| 1:5 | ×333.1 | 99.0 |
| 1:10 | ×339.8 | 99.5 |

As shown in Table 34, a high expansion culturing rate and a high NK cell content rate (%) were obtained by 5-fold or 10-fold increasing the ratio of RN-T AIC to be added.

That is, it was made clear that proliferability of a NK cell was increased RN-T AIC amount-dependently, and it was made clear that RN-T AIC was preferably used in culture of a NK cell.

Example 19

Measurement of Cytotoxic Activity after Freezing/Thawing of NK Cell Cultured Using OK-432 and AIC (1) Expansion Culture of Anti-CD3 Antibody/RetroNectin-Stimulated T Cell In the same manner as that of Example 14-(1), expansion culture of an anti-CD3 antibody/RetroNectin-stimulated T cell was performed.

(2) Preparation of AIC Using RN-T

Using the RN-T prepared in Example 19-(1), AIC was prepared in the same manner as that of Example 14-(2).

(3) Expansion Culture of NK Cell Population

In the same manner as that of Example 14-(3), expansion culture of a NK cell population was performed.

(4) Storage of NK Cell

The cells on sixteenth day prepared in Example 19-(3) were adjusted to $1 \times 10^8$ cells/vial using CP-1/HSA and stored in liquid nitrogen, in the same way as in Example 1-(1).

(5) Thawing of NK Cell

The cells which had been freezing-stored in Example 19-(4) were rapidly thawed in a water bath at 37° C., and washed using GT-T502. These cells were adjusted to about $2 \times 10^6$ cells/mL using 0.2HGT-T503, and each 4 mL of the suspension was added to a 12-well cell culture plate. IL-2 was added to the plate in an amount of 0 (non-addition group), 200 or 1000 U/mL, and the plate was incubated at 37° C. overnight in the presence of 5% $CO_2$.

(6) Measurement of Cytotoxic Activity of NK Cell

Using the cells prepared in Example 19-(3) and (5), cytotoxic activity on target cells A549 and A375 before and after freezing storage was measured in the same manner as that of Example 1-(5) except that the E/T ratio was 10. Results are shown in Table 35.

TABLE 35

| Cytotoxic activity measurement day | | IL-2 addition concentration (U/mL) | Cytotoxic activity (%) | |
|---|---|---|---|---|
| | | | A549 | A375 |
| Before freezing | — | — | 61.8 | 52.5 |
| After freezing | Thawing day | 0 | 23.8 | 27.7 |
| | One day after thawing | 0 | 60.9 | 53.4 |
| | | 200 | 71.7 | 86.3 |
| | | 1000 | 83.0 | 75.1 |

As shown in Table 35, a NK cell transiently exhibited reduced cytotoxic activity immediately after freezing/thawing. However, after cultured overnight, the NK cell exhibited cytotoxic activity equivalent as compared with immediately after freezing/thawing. The activity was further enhanced by culture with addition of IL-2, and high cytotoxic activity exceeding the activity before freezing was exhibited.

That is, it was made clear that the activity was recovered by culturing a NK cell after freezing and thawing overnight, and the cytotoxic activity was further increased by adding IL-2.

Example 20

Culture of NK Cell Using OK-432 and Mild Heat-Treated Cell (Comparison of Mild Heat Treatment Condition-1)

(1) Preparation of Anti-Human CD3 Antibody and RetroNectin-Immobilized Plate

In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of Mild Heat-Treated Cell Using RN-T

The RN-T prepared in Example 20-(2) was mild heat-treated in the same manner as that of Example 16-(3) to prepare a mild heat-treated RN-T, provided that the temperature for mild heat treatment was 45 and 48° C., the treatment time was 0.5, 1, 2 or 4 hours, and the cell concentration for treatment was adjusted to $2 \times 10^6$ cells/mL with 0.8HCellGro.

(4) Expansion Culture of NK Cell Population

Expansion culture of a NK cell was performed in the same manner as that of Example 12-(4) except that a group in which mild heat-treated RN-T was used in place of AIC and OK-432 was added, and a group in which only OK-432 was added (hereinafter, referred to as control group) were set. The operations on first and thirteenth days in Example 12-(4) were performed on second and fourteenth days in the present Example, respectively. On sixteenth day after culture initiation, the number of live cells was measured by a trypan blue staining method and the number was compared with the cell number at culture initiation to calculate an expansion culturing rate. Further, in the same manner as that of Example 1-(4), a NK cell content rate was analyzed. Results are shown in Table 36.

TABLE 36

| Mild heat-treated RN-T conditions | | Expansion culturing rate | NK cell content rate (%) |
|---|---|---|---|
| Temperature (° C.) | Time | | |
| 45 | 0.5 | ×142.2 | 92.5 |
| | 1.0 | ×160.1 | 93.1 |
| | 2.0 | ×126.5 | 87.9 |
| | 4.0 | ×74.2 | 82.1 |
| 48 | 0.5 | ×126.5 | 90.9 |
| | 1.0 | ×64.4 | 80.7 |
| | 2.0 | ×84.9 | 86.1 |
| | 4.0 | ×116.2 | 90.0 |
| Control group | — | ×35.8 | 71.8 |

As shown in Table 36, a higher expansion culturing rate and a higher NK cell content rate (%) were obtained by using OK-432 and mild heat-treated RN-T, as compared with a mild heat-treated cell-non-addition group (control group). The temperature and time for mild heat treatment were not particularly limited, and the desired effect was confirmed in a wide range of treatment conditions.

That is, it was made clear that a high purity NK cell was obtained at a high expansion culturing rate by combining OK-432 and RN-T mild heat-treated cell in culture of a NK cell.

Example 21

Culture of NK Cell Using OK-432 and Mild Heat-Treated Cell (Comparison of Mild Heat Treatment Condition-2)

(1) Preparation of Anti-Human CD3 Antibody and RetroNectin-Immobilized Plate

In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of Mild Heat-Treated Cell Using RN-T

The RN-T prepared in Example 21-(2) was suspended to 1 or $2 \times 10^6$ cells/mL using GT-T551. The prepared cell liquid (50 mL) was transferred to a 200 mL separation bag (manufactured by TERUMO CORPORATION), and mild heat treatment was performed using a water bath at 45° C. for 0.25 or 0.5 hour, provided that under the condition of a cell concentration of $2 \times 10^6$ cells/mL, only mild heat treatment at 45° C. for 0.5 hour was performed. The cell liquid after mild heat treatment was recovered into a 50 mL conical tube (manufactured by Corning Incorporated), and centrifuged at 440×g and room temperature for 5 minutes. After centrifugation, the supernatant was removed, and cells were suspended in 0.8HCellGro at $2 \times 10^6$ cells/mL.

(4) Expansion Culture of NK Cell Population

Expansion culture of a NK cell was performed in the same manner as that of Example 12-(4) except that at culture initiation, each 0.95 mL/well of a Responder cell and the mild heat-treated RN-T prepared in Example 21-(3) were added to a 12-well cell culture plate, so that the total was 1.9 mL/well. On third day, 1.9 mL of 0.8HCellGro was added to each well. On seventh day, a cell liquid of each well was 6-fold diluted using 0.8HCellGro, 1.4 mL of the cell liquid was transferred to a new T25 cell culture flask (manufactured by FALCON, or manufacture by Corning Incorporated), and the flask was stood to perform culture. The same subculturing operation was performed on eleventh day and fourteenth day, and culture was continued until seventeenth day. The dilutions of the cell liquids on eleventh day and fourteenth day were 5-fold dilution with 0.8HGT-T502, and 3-fold dilution with 0.29HGT-T502, respectively. On seventeenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 37.

TABLE 37

| Mild heat treatment conditions | | | Expansion culturing rate | NK cell content rate (%) |
|---|---|---|---|---|
| Temperature (° C.) | Time | Cell concentration at treatment (×10$^6$ cells/mL) | | |
| 45 | 0.25 | 1 | ×142.2 | 72.9 |
| | 0.5 | 1 | ×147.6 | 90.4 |
| | | 2 | ×107.1 | 92.5 |
| Control group | | | ×0.45 | 32.5 |

As shown in Table 37, in a group in which OK-432 and mild heat-treated RN-T were added, the desired effect was confirmed under a wide range of treatment conditions, without particularly limiting the time and the cell concentration for mild heat treatment, as compared with a control group in which only OK-432 was added and a mild heat-treated cell was not added.

That is, it was made clear that a high expansion culturing rate and a high purity NK cell were obtained by combining OK-432 and a RN-T mild heat-treated cell in culture of a NK cell.

Example 22

Measurement of Multifunction Ability Using NK Cell (1) Preparation of Anti-Human CD3 Antibody and RetroNectin-Immobilized Plate In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of AIC Using RN-T

In the same manner as that of Example 18-(3), preparation of AIC was performed.

(4) Expansion Culture of NK Cell Population

Expansion culture of a NK cell was performed in the same manner as that of Example 21-(4) except that the AIC prepared in Example 22-(3) was used in place of a mild heat-treated cell, the operation on third day in Example 21-(4) was performed on second day in the present Example, and culture was continued until twenty-second day.

(5) Measurement of Multifunction Ability of NK Cell

After the cells on twenty-second day after culture initiation prepared in Example 22-(4) were diluted with 5HRPMI to $3 \times 10^6$ cells/mL as an effector cell, each 100 µL/well of the dilution was dispensed into each well of a 96-well cell culture plate. Each 100 µL/well of a target cell (K562) which had been adjusted to $1 \times 10^6$ cells/mL was added to each of the plate. At this time, the ratio of an effector cell (E) to a target cell (T), that is, E/T ratio was 3. Each 1 µL/well of a PE/Cy5-labeled mouse CD107a antibody (manufactured by abcam plc.) was added, and the plate was incubated at 37° C. for 1 hour. Further, after Brefeldin A (manufacture by Sigma Corporation) was added in a final concentration of 10 µg/mL, the plate was incubated at 37° C. for 3 hours. The plate after incubation was centrifuged at 250×g for 5 minutes, the supernatant was removed, the cells were suspended in 1% BSA/DPBS, and an ECD-labeled mouse anti-human CD3 antibody and a PC7-labeled mouse anti-human CD56 antibody (all manufactured by Beckman Coulter Inc.) were added. Similarly, as a negative control, FITC-labeled mouse IgG1/RD1-labeled mouse IgG1/PC5-labeled mouse IgG1 (manufactured by Beckman Coulter Inc.) was added to a portion of each cell population. After each antibody was added, the cells were incubated at 4° C. for 30 minutes and, thereafter, were washed with 0.1% BSA/DPBS. For measuring an intracellular cytokine, IntraPrep (manufactured by Beckman Coulter Inc.) was used. After IntraPrepReagent was used for the purpose of immobilization and membrane permeabilization treatment of cells, a FITC-labeled mouse anti-human TNF-α antibody (manufactured by BD Biosciences) and a PE-labeled mouse anti-human IFN-γ antibody (manufactured by Beckman Coulter Inc.) were added. After each antibody was added, incubation was performed at room temperature for 15 minutes. The plate after incubation was centrifuged at 250×g for 5 minutes, the supernatant was removed and, thereafter, the cells were suspended with 0.1% BSA/DPBS. These cells were subjected to flow cytometry, CD107a, TNF-α and IFN-γ-positive ratios in a NK cell were calculated, wherein a CD3-negative and CD56-positive cell group was regarded as a NK cell, and the multifunction ability was analyzed. In the analysis of multifunction ability, a cell expressing three of CD107a, TNF-α and IFN-γ at the same time was regarded as "+++", a cell expressing two of them was regarded as "++", a cell expressing one of them was regarded as "+", and a cell expressing none of them was regarded as "−". Results are shown in Table 38.

TABLE 38

| CD3−CD56+CELL Multifunctional ability | Positive rate (%) | |
|---|---|---|
| | at addition of no K562 | at addition of K562 |
| +++ | 4.4 | 5.7 |
| ++ | 5.5 | 10.0 |
| + | 20.4 | 30.9 |
| − | 69.7 | 53.4 |

As shown in Table 38, it was confirmed that the multifunctional ability was increased by mixing a NK cell with a target cell.

That is, it was made clear that a NK cell cultured by the culture process of the present invention had high multifunctionality, and the function was further increased, when mixed with a tumor cell, and it was shown that the NK cell was a NK cell having high functionality.

Example 23

Culture of NK Cell Using OK-432 and Mitomycin-Treated Cell (1) Preparation of Anti-Human CD3 Antibody and RetroNectin-Immobilized Plate In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of Mitomycin C-Treated Cell Using RN-T

The RN-T prepared in Example 23-(2) was suspended at $2 \times 10^6$ cells/mL using 5HRPMI. The prepared cell liquid (5 mL) was transferred to a 15 mL conical tube (manufactured by Corning Incorporated), mitomycin C (product name: Mitomycin Kyowa S, manufactured by Kyowa Hakko Kirin Co., Ltd.) was added in a final concentration of 10 or 20 µg/mL, and this was incubated at 37° C. for 0.5 or 1.0 hour. After the reaction, centrifugation was performed at 440×g and room temperature for 5 minutes. After centrifugation, the supernatant was removed, and cells were similarly washed two times using 5HRPMI, and adjusted to $2 \times 10^6$ cells/mL using 0.8% HCellGro.

(4) Expansion Culture of NK Cell Population

Expansion culture of a NK cell was performed in the same manner as that of Example 21-(4) except that a mitomycin C-treated cell condition group was set in place of a mild heat-treated cell. And, in a control group, only OK-432 was added. The operation on third day in Example 21-(4) was performed on first day in the present Example, and culture was continued until eighteenth day. On eighteenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 39.

TABLE 39

| Mitomycin C treatment condition | | Expansion culturing rate | NK cell content rate (%) |
|---|---|---|---|
| Treatment concentration (μg/mL) | Time (H) | | |
| 10 | 0.5 | ×165.6 | 96.7 |
|  | 1.0 | ×142.2 | 95.9 |
| 20 | 0.5 | ×182.7 | 97.0 |
|  | 1.0 | ×141.3 | 92.6 |
| Control group | | ×89.1 | 74.1 |

As shown in Table 39, in a group in which OK-432 and mitomycin C-treated RN-T were added, the desired effect was confirmed under a wide range of treatment conditions without particular limitation of the concentration and the time for mitomycin C treatment, as compared with a control group in which only OK-432 was added and a mitomycin C-treated cell was not added.

That is, it was made clear that a high purity NK cell was obtained at a high expansion culturing rate by combining OK-432 and a mitomycin C-treated RN-T cell in culture of a NK cell.

Example 24

Culture of NK Cell Using OK-432 and AIC (Comparison of AIC-Treated Cells)

(1) Preparation of Anti-Human CD3 Antibody and RetroNectin-Immobilized Plate

In the same manner as that of Example 18-(1), an anti-human CD3 antibody and RetroNectin-immobilized plate was prepared. A plate on which only an anti-human CD3 antibody was immobilized was also manufactured.

(2) Expansion Culture of Anti-CD3 Antibody/RetroNectin-Stimulated T Cell and Anti-CD3 Antibody-Stimulated T Cell In the same manner as that of Example 3-(2), expansion culture of RN-T was performed. Similarly, using the plate on which only an anti-human CD3 antibody had been immobilized prepared in Example 24-(1), a T cell which was expansion-cultured by anti-CD3 antibody stimulation (hereinafter, referred to as OKT3-T) was also prepared.

(3) Preparation of AIC Using RN-T and OKT3-T

In the same manner as that of Example 18-(3), preparation of RN-T AIC was performed. At this time, using the OKT3-T prepared in Example 24-(2), AIC was similarly prepared (hereinafter, referred to as OKT3-T AIC).

(4) Expansion Culture of NK Cell Population

Expansion culture of a NK cell was performed in the same manner as that of Example 23-(4) except that a group in which the RN-T AIC or OKT3-T AIC prepared in Example 24-(3) or PBMC AIC prepared in the same manner as that of Example 1-(2) was added on the first day was also set. Also, on seventh day after culture initiation, each $1 \times 10^6$ cells/flask of the RN-T AIC, OKT3-T AIC or PBMC AIC was added. A group in which only OK-432 was added was used as a control group. On eighteenth day after culture initiation, the number of live cells was measured by a trypan blue staining method, and the number was compared with the cell number at culture initiation to calculate an expansion culturing rate. Further, in the same manner as that of Example 1-(4), a NK cell content rate was analyzed. Results are shown in Table 40.

TABLE 40

| AIC used | Expansion culturing ratio | NK cell content rate (%) |
|---|---|---|
| RN-T AIC | ×268.9 | 98.3 |
| OKT3-T AIC | ×270.0 | 96.3 |
| PBMC AIC | ×200.2 | 90.6 |
| Control group | ×111.4 | 71.7 |

As shown in Table 40, a higher expansion culturing rate and a higher NK cell content rate were obtained in a group in which RN-T AIC or OKT3-T AIC was used, as compared with the case where PBMC AIC was used.

That is, it was made clear that a high purity NK cell was obtained at a high expansion culturing rate by using OKT3-T or RN-T as AIC in culture of a NK cell.

Use of PBMC for preparing AIC necessitates a large amount of blood. However, a highly functional NK cell having a higher purity can be obtained in a large amount, while reducing a physical burden on a patient itself by using OKT3-T or RN-T expansion-cultured from a small amount of blood. Hence, according to the present invention, it becomes possible to utilize NK expansion culture technique having a smaller physical burden.

Example 25

Culture of NK Cell Using OK-432 and Mild Heat-Treated Cell (Comparison of Mild Heat-Treated Cell)

(1) Preparation of Anti-Human CD3 Antibody and RetroNectin-Immobilized Plate

In the same manner as that of Example 24-(1), an anti-human CD3 antibody and RetroNectin-immobilized plate, and a plate on which only an anti-human CD3 antibody was immobilized were manufactured.

(2) Expansion Culture of Anti-CD3 Antibody/RetroNectin-Stimulated T Cell and Anti-CD3 Antibody-Stimulated T Cell In the same manner as that of Example 24-(2), expansion culture of RN-T and OKT3-T was performed.

(3) Preparation of Mild Heat-Treated Cell Using RN-T and OKT3-T

In the same manner as that of Example 16-(3), preparation of a mild heat-treated cell was performed. At this time, using the OKT3-T prepared in Example 25-(2), a mild heat-treated cell was similarly prepared (hereinafter, referred to as mild heat-treated OKT3-T cell).

(4) Expansion Culture of NK Cell Population

Expansion culture of a NK cell was performed in the same manner as that of Example 24-(4) except that the mild heat-treated RN-T cell and a mild heat-treated OKT3-T cell prepared in Example 25-(3) were used, or a group in which only OK432 was added as a control group was also set. On eighteenth day after culture initiation, the number of live cells was measured by a trypan blue staining method, and the number was compared with the cell number at culture initiation to calculate an expansion culturing rate. Further, in the same manner as that of Example 9-(6), a NK cell content rate and a CD16-positive CD56-positive cell content rate were analyzed. Results are shown in Table 41.

TABLE 41

| Mild heat-treated cell used | Expansion culturing rate | NK cell content rate (%) | CD16+CD56+ cell content rate (%) |
|---|---|---|---|
| Mild heat-treated RN-T | ×185.6 | 83.5 | 77.0 |
| Mild heat-treated OKT3-T | ×189.0 | 72.6 | 68.2 |
| Control group | ×111.4 | 71.7 | 64.9 |

As shown in Table 41, a higher expansion culturing rate and a higher NK cell content rate, as well as a higher 16-positive CD56-positive cell content rate were obtained in a group using a mild heat-treated RN-T cell, as compared with the case where a mild heat-treated OKT3-T cell was used.

That is, it was made clear that a high purity and highly functional NK cell was obtained at a higher expansion culturing rate by using RN-T as a mild heat cell in culture of a NK cell.

Example 26

Assessment of Anti-Tumor Activity of Human NK Cell Using Immunodeficient Mouse Heterogeneous Tumor Model (1) Mouse and Group Constitution Female 16 NOD/scid mice (manufactured by CLEA Japan, Inc.), 7 weeks old, were made so as to have group constitution shown in the following Table 42. Human NK cell-administered groups are B to D groups. In each group, N=4.

TABLE 42

| A group | Group of administering 4% HSA-containing physiological saline into tail vein (control) |
| B group | Group of administering human NK cell into tail vein |
| C group | Group of administering IFNα-treated human NK cell into tail vein |
| D group | Group of administering human NK cell intratumorally |

(2) Administration of Anti-Asialo GM1 Antibody

It is known that treatment with an anti-asialo GM1 antibody removes a mouse NK cell and enhances engraftment of a human cell in a NOD/scid mouse. On a day before inoculation with A549 and on a day before first administration of a human NK cell, 20 μL of an anti-asialo GM1 antibody solution (manufactured by Wako Pure Chemical Industries, Ltd.) was diluted with 0.38 mL of a 0.4% HSA-containing physiological saline (manufactured by Otsuka Pharmaceutical Co., Ltd.), and the all amount was intraperitoneally administered to the mouse.

(3) Heterogeneous Tumor Model of NOD/scid-A549

All the NOD/scid mouse groups were irradiated with an X-ray (3 Gy), a hair of a right groin area was shaved about 9 square centimeters under anesthesia, and 0.1 mL of A549 which had been adjusted to $5 \times 10^7$ cells/mL in a RPMI1640 medium was subcutaneously inoculated.

(4) Culture/Preparation of Human NK Cell to be Administered

Expansion culture of a human NK cell was performed in the same manner as that of Example 14-(3) except that on sixteenth day after culture initiation, IL-2 was added in a final concentration of 200 U/mL and, on eighteenth day, 338 mL of a cell liquid in CultiLife Eva was adjusted to a total liquid amount of 675 mL using 0.2% HSA/GT-T503, thereafter, IL-2 was added in a final concentration of 200 U/mL, and the cell liquid was transferred to CultiLife Eva. Culture was continued until twenty-first day.

(5) Administration of Human NK Cell

A total of three times of 7 days, 9 days and 12 days after tumor inoculation, the following treatment was performed.

To the A group was administered 0.3 mL of a 4% HSA-containing physiological saline, into a tail vein. To the B group was administered 0.3 mL of a human NK cell which had been adjusted to $3.33 \times 10^7$ cells/mL with a 4% HSA-containing physiological saline, into a tail vein. A human NK cell which had been IFNα-treated in the same manner as that of Example (15)-2 was adjusted to $3.33 \times 10^7$ cells/mL with a 4% HSA-containing physiological saline, and 0.3 mL of the cell liquid was administered to the C group into a tail vein. To the D group was intratumorally administered 0.1 mL of a human NK cell which had been adjusted to $1.00 \times 10^8$ cells/mL with a 4% HSA-containing physiological saline.

(6) Assessment of Anti-Tumor Activity after Administration of Human NK Cell in Heterogeneous Tumor Model of NOD/scid-A549

On forty-second day after tumor inoculation, a tumor volume in each individual was measured using an electronic slide caliper. Results thereof are shown in Table 43.

A tumor volume was calculated using the following equation (3):

[Mathematic 3]

$$\text{Tumor volume}(mm^3) = R1 \times R1 \times R2 \times 0.5 \qquad \text{Equation (3)}$$

wherein R1 represents a short diameter, and R2 represents a long diameter.

TABLE 43

| | Administration cell | Administration site | Tumor size (mm³) | Standard error |
|---|---|---|---|---|
| A group | None (control) | Tail vein | 1793.5 | 212.2 |
| B group | Human NK cell | Tail vein | 1432.3 | 225.3 |
| C group | Human NK cell (IFNα treatment) | Tail vein | 1286.1 | 415.5 |
| D group | Human NK cell | Intratumoral administration | 543.3 | 327.1 |

Also, a tumor weight on forty-second day after tumor inoculation in each individual was measured. Results are shown in Table 44.

TABLE 44

| | Administration cell | Administration site | Tumor weight (g) | Standard error |
|---|---|---|---|---|
| A group | None (control) | Tail vein | 1.31 | 0.09 |
| B group | Human NK cell | Tail vein | 1.22 | 0.22 |
| C group | Human NK cell (IFNα treatment) | Tail vein | 1.27 | 0.26 |
| D group | Human NK cell | Intratumoral administration | 0.38 | 0.30 |

As shown in Tables 43 and 44, it was made clear that, in a group in which a human NK cell expansion-cultured by the culture process of the present invention had been administered, both of a tumor volume and a tumor weight were smaller, and a higher anti-tumor activity was shown, as compared with a control group (A group). This effect was enhanced by treating a human NK cell to be administered with IFNα. When intratumoral administration was performed, more remarkable anti-tumor activity was exhibited, and high effectiveness of a human NK cell expansion-cultured by the culture process of the present invention was recognized.

From the above results, it was confirmed that treatment by administration of a human NK cell cultured by the culture process of the present invention was extremely effective.

Example 27

Assessment of Metastasis Inhibitory Activity of Human NK Cell Using Immunodeficient Mouse Heterogeneous Tumor Metastasis Model (1) Mouse and Group Constitution Female 20 NOD/scid mice, 7 weeks old, were made so as to have group constitution shown in the following Table 45. Human NK cell-administered groups are B to E groups. In each group, N=4.

TABLE 45

| A group | Group of administering 4% HSA-containing physiological saline into tail vein (control) |
|---------|---|
| B group | Group of administering human NK cell into tail vein |
| C group | Group of administering IFNα-treated human NK cell into tail vein |
| D group | Group of administering IL-2-treated human NK cell into tail vein |
| E GROUP | Group of administering IFNα and IL-2-treated human NK cell into tail vein |

(2) Administration of Anti-Asialo GM1 Antibody

On a day before A549 inoculation, 20 μL of an anti-asialo GM1 antibody solution was diluted with 0.38 mL of a 0.4% HSA-containing physiological saline, and the all amount was intraperioneally administered to the mouse.

(3) Heterogeneous Tumor Metastasis Model of NOD/scid-A549

All the NOD/scid mouse groups were irradiated with an X-ray (3 Gy), and 0.3 mL of A549 which had been adjusted to $6.6 \times 10^6$ cells/mL in a RPMI1640 medium was administered into a tail vein.

(4) Culture of Human NK Cell

Expansion culture of a NK cell was performed in the same manner as that of Example 26-(4) except that on twenty-first day after culture initiation, 338 mL of a cell liquid in CultiLife Eva was adjusted to a total liquid amount of 675 mL using 0.2% HSA/GT-T503 and, thereafter, IL-2 was added in a final concentration of 200 U/mL. Culture was continued until twenty-third day.

(5) Preparation of Cell for Administration groups in which cells on eighteenth day, twenty-first day or twenty-third day after culture initiation were treated with IFNα were made (IFN-α-treated NK cell), in the same manner as that of Example 15-(2) except that IFNα treatment was performed using a cell liquid which had been adjusted to $5 \times 10^7$ cells/mL with GT-T503. Similarly, the condition under which IL-2 was added in a final concentration of 1000 U/mL (IL-2-treated NK cell) or IFN-α and IL-2 were added in each final concentration of 1000 U/mL (IFNα+IL-2-treated NK cell) was set, and each group was allowed to stand in a 5% $CO_2$ incubator at 37° C. for 1 hour. Additionally, the condition under which cells were only allowed to stand in a 5% $CO_2$ incubator at 37° C. for 1 hour was set.

A human NK cell and each treated human NK cell were adjusted to $3.33 \times 10^7$ cells/mL using a 4% HSA-containing physiological saline.

(6) Administration of Human NK Cell

A total of three times of 3 days, 6 days and after 8 days after tumor administration, the following treatment was performed.

To the A group was administered 0.3 mL of a 4% HSA-containing physiological saline, into a tail vein. To the B group was administered a human NK cell, to the C group was administered an IFNα-treated human NK cell, to the D group was administered an IL-2-treated human NK cell, and to the E group was administered an IFNα+IL-2-treated human NK cell in each 0.3 mL, into a tail vein.

(7) Assessment of Anti-Tumor Activity after Administration Of Human NK Cell in Heterogeneous Tumor Metastasis Model of NOD/scid-A549

A hepatic weight on thirty-first day after tumor administration in each individual was measured. Results are shown in Table 46.

TABLE 46

| | Administration cell | Administration site | Hepatic weight (g) | Standard error |
|---|---|---|---|---|
| A group | None (control) | Tail vein | 1.859 | 0.248 |
| B group | Human NK cell | Tail vein | 1.293 | 0.236 |
| C group | Human NK cell (IFNα treatment) | Tail vein | 1.290 | 0.158 |
| D group | Human NK cell (IL-2 treatment) | Tail vein | 1.286 | 0.145 |
| E group | Human NK cell (IFNα and IL-2 treatment) | Tail vein | 1.167 | 0.112 |

As shown in Table 46, it was made clear that, a group of administering a human NK cell expansion-cultured by the culture process of the present invention had a lower hepatic weight and higher metastasis inhibitory activity, as compared with a control group. From the above results, it was confirmed that treatment by administration of a human NK cell cultured by the culture process of the present invention was extremely effective.

Example 28

Comparison Between NK Cell Expansion Culture Process Using OK-432 and AIC, and NK Cell Expansion Culture Process Using OKT-3

(1) Preparation of Anti-Human CD3 Antibody and RetroNectin-Immobilized Plate

In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of RN-T AIC

In the same manner as that of Example 18-(3), RN-T AIC was prepared.

(4) Expansion Culture of NK Cell Population Using OK-432 and AIC

In the same manner as that of Example 1-(1), PBMC was separated, and used in expansion culture of a NK cell without freezing storage. The separated PBMC was adjusted to $2 \times 10^6$ cells with 0.8HCellGro, and each 0.25 mL of the cell liquid was added to a 48-well cell culture plate (manufactured by Corning Incorporated). Each 0.25 mL of the RN-T AIC prepared in Example 28-(3) was added, OK-432 was added in a final concentration of 0.05 KE/mL, IL-2 was added in a final concentration of 200 U/mL, and culture was initiated.

On second day after culture initiation, each 0.5 mL of 0.8HCellGro was added to each well of the plate, and IL-2 was added in a final concentration of 200 U/mL. On fourth day, IL-2 was added to each well in a final concentration of 200 U/mL. On seventh day, a cell liquid of each well was 6-fold diluted using 0.8HCellGro, and 1.596 mL of the diluted cell liquid was transferred to a new 24-well cell culture plate. On eleventh day, the cell liquid of each well was 5-fold diluted using 0.8HGT-T502, and 1.330 mL of the diluted cell liquid was transferred to a new 24-well cell culture plate. On fourteenth day, the cell liquid was diluted 3-fold using 0.3HGT-T502, 2.0 mL of the diluted cell liquid was transferred to a new 24-well cell culture plate, and culture was continued until eighteenth day. In the present Example, hereinafter, the present process is referred to as A process.

(5) Expansion Culture of NK Cell Population Using OKT-3 (Reference Publication: Alici et al., BLOOD, 2008, Vol. 111, p. 3155-3162, and USA Laid-Open Publication No. 2003/0068306)

In the same manner as that of Example 1-(1), PBMC was separated, and used in expansion culture of a NK cell without freezing storage. The separated PBMC was adjusted to 0.5× $10^6$ cells/mL with 5HCellGro, and each 1 mL of the cell liquid was added to a 48-well cell culture plate. OKT-3 was added in a final concentration of 10 ng/mL, IL-2 was added in a final concentration of 500 U/mL, and culture was initiated.

On fifth day after culture initiation, after cells were centrifuged at 500×g for 5 minutes, the supernatant was discarded, and cells were suspended with 2 mL of 5HCellGro. After the all amount was added to a new 24-well cell culture plate, IL-2 was added in a final concentration of 500 U/mL. On seventh day, ninth day, eleventh day, thirteenth day and fifteenth day after culture initiation, 1 mL of a cell liquid was transferred to a new 24-well cell culture plate, 1 mL of 5HCellGro was added, and, thereafter, IL-2 was added in a final concentration of 500 U/mL. Culture was continued until eighteenth day. In the present Example, hereinafter, the present process is referred to as B process.

(6) Analysis of Surface Antigen

In expansion culture of a NK cell population of Example 28-(4) and Example 28-(5), in the same manner as that of Example 14-(4), a T cell content rate, a NK cell content rate, a CD16-positive CD56-positive cell content rate and a NKG2D-positive CD56-positive cell content rate were analyzed. Results are shown in Table 47.

TABLE 47

| Culture process | Cell content rate (%) | | | |
|---|---|---|---|---|
| | CD3+ CD56− | CD3− CD56+ | CD16+ CD56+ | NKG2D+ CD56+ |
| A process | 0.8 | 98.7 | 96.5 | 91.2 |
| B process | 40.4 | 39.5 | 41.5 | 63.8 |

As shown in Table 47, in the A process, the rate of a NK cell after culture was remarkably higher, and CD16 and NKG2D were expressed at a further higher rate, and it was confirmed that a highly functional NK cell expressing a CD16 molecule which played an important role in exerting antibody-dependent cell-mediated cytotoxicity and a highly functional NK cell exhibiting high cytotoxic activity through NKG2D were contained in a high proportion.

(7) Measurement of Cytotoxic Activity

Regarding the cells on eighteenth day after culture initiation prepared in Example 28-(4) and Example 28-(5), cytotoxic activity was measured in the same manner as that of Example 14-(5). Results are shown in Table 48.

TABLE 48

| Target cell | E/T ratio | Cytotoxic activity (%) | |
|---|---|---|---|
| | | A process | B process |
| K562 | 10 | 78.9 | 71.8 |
| | 3 | 79.8 | 69.3 |
| | 1 | 46.9 | 37.4 |
| | 0.3 | 21.0 | 14.4 |
| A549 | 10 | 68.8 | 13.3 |
| | 3 | 54.5 | 11.1 |
| | 1 | 28.0 | 3.6 |
| | 0.3 | 14.3 | 0.6 |

As shown in Table 48, it was made clear that a cell population obtained by the A process exhibited higher cytotoxic activity on various target cells than that of a cell population obtained by the B process. The difference in the activity was remarkably confirmed for an MHC class I-expressing cell strain A549, and it was confirmed that the cell population was a highly functional NK cell exerting cytotoxic activity on a variety of cancer cell strains.

That is, it was made clear that a NK cell population expansion-cultured by the process of the present invention had a higher purity of a CD3-negative CD56-positive cell, and expressed CD16 and NKG2D at a higher rate and was a highly functional NK cell population having higher cytotoxicity, as compared with other culture processes.

Example 29

Expansion Culture of Purified CD3-Negative CD56-Positive Cell (1) Preparation of Anti-Human CD3 Antibody and RetroNectin-Immobilized Plate In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of RN-T AIC

In the same manner as that of Example 18-(3), RN-T AIC was prepared.

(4) Purification of CD3-Negative CD56-Positive Cell

In the same manner as that of Example 1-(1), PBMC was separated, and used for purifying a CD3-negative CD56-positive cell without freezing storage. Then, the PBMC at $5 \times 10^7$ cells was suspended in DPBS (hereinafter, referred to as selection buffer) containing 0.4 mL of 0.5% BSA and 2 mM ethylenediaminetetraacetic acid (EDTA, manufactured by Nacalai Tesque, Inc.), 0.1 mL CD3 microbeads (manufactured by Miltenyi Biotec, Inc.) were added, and the suspension was incubated at 4° C. for 15 minutes. After 5 mL of the selection buffer was added followed by centrifugation at 300×g for 10 minutes, the supernatant was removed, and the cells were suspended in 0.5 mL of the selection buffer. The cell suspension was passed through an LS column (manufactured by Miltenyi Biotec, Inc.) which had been fixed in the magnetic field in advance and through which 3 mL of the selection buffer had been passed, and the column was washed three times with 3 mL of the selection buffer, thereby, fractions not bound to the column were collected to obtain 3.5× $10^7$ CD3-negative cells.

The resulting CD3-negative cells were suspended in 0.28 mL of the selection buffer, 70 µL of CD56 microbeads (manufactured by Miltenyi Biotec, Inc.) were added, and the suspension was incubated at 4° C. for 15 minutes. After the selection buffer (5 mL) was added followed by centrifugation at 300×g for 10 minutes, the supernatant was removed, and the cells were suspended in 0.5 mL of the selection buffer. The cell suspension was passed through an MS column (manufactured by Miltenyi Biotec, Inc.) which had been fixed in the magnetic field in advance and through which 0.5 mL of the selection buffer had been passed, and the column was washed three times with 0.5 mL of the selection buffer. The column was removed from the magnetic field, and 1 mL of the selection buffer was passed through the column to obtain $7.2 \times 10^6$ CD3-negative CD56-positive cells.

(5) Expansion Culture of NK Cell Population Using OK-432 and AIC

The CD3-negative CD56-positive cell purified in Example 29-(4) was adjusted to $2 \times 10^6$ cells with 0.8HCellGro, and each 0.25 mL of the suspension was added to a 48-well cell culture plate. AIC-addition condition and AIC-non-addition condition were set. In the case of AIC-addition condition, each 0.25 mL of the RN-T AIC prepared in Example 29-(3) was added. In the case of AIC-non-addition condition, each 0.25 mL of 0.8HCellGro was added. OK-432 was added in a final concentration of 0.05 KE/mL, IL-2 was added in a final concentration of 200 U/mL, and culture was initiated.

On second day after culture initiation and thereafter, culture was performed in the same way as in Example 28-(4).

In the present Example, hereinafter, the present process is referred to as A' process.

(6) Expansion Culture of NK Cell Population Using X-VIVO 10 Medium (Manufactured by Lonza)
(Reference Publication: Koehl et al., BLOOD Cells, Molecules, and Diseases, 2004, vol. 33, p. 261-266)

The CD3-negative CD56-positive cell purified in Example 29-(4) was adjusted to $1 \times 10^6$ cells/mL with an X-VIVO 10 medium containing 10% human type AB serum (hereinafter, referred to as 10HX-VIVO), and each 0.5 mL of the suspension was added to a 48-well cell culture plate. IL-2 was added in a final concentration of 1000 U/mL, and culture was initiated.

On third day after culture initiation, 0.5 mL of 10HX-VIVO was added, and IL-2 was added in a final concentration of 1000 U/mL. On sixth day after culture initiation, the all amount of a cell liquid was transferred to a new 24-well cell culture plate, 1 mL of 10HX-VIVO was added, and IL-2 was added in a final concentration of 1000 U/mL. On ninth day, on twelfth day and on fifteenth day, 1 mL of the culture supernatant was removed, 1 mL of 10HX-VIVO was added and, thereafter, IL-2 was added in a final concentration of 1000 U/mL. Culture was continued until eighteenth day. In the present Example, hereinafter, the present process is referred to as C process.

(7) Measurement of Cell Number and Analysis of Surface Antigen

In expansion culture of a NK cell population of Example 29-(5) and Example 29-(6), on eighteenth day after culture initiation, the number of live cells was measured by a trypan blue staining method, and the number was compared with the cell number at culture initiation to calculate an expansion culturing rate. In addition, in the same manner as that of Example 14-(4), a T cell content rate, a NK cell content rate, a CD16-positive CD56-positive cell content rate and a NKG2D-positive CD56-positive cell content rate were analyzed. Results are shown in Table 49.

TABLE 49

| Culture process | Expansion culturing rate | CD3+ CD56− | CD3− CD56+ | CD16+ CD56+ | NKG2D+ CD56+ |
|---|---|---|---|---|---|
| | | Cell content rate (%) | | | |
| A' process (AIC−) | ×108.8 | 0.1 | 99.5 | 98.3 | 98.9 |
| A' process (AIC+) | ×127.0 | 0.0 | 99.6 | 96.6 | 98.7 |
| C process | ×2.5 | 0.1 | 99.5 | 84.8 | 95.6 |

As shown in Table 49, an expansion culturing rate in culture using a purified peripheral blood CD3-negative CD56-positive cell was remarkably higher in an expansion culture process using OK-432 (A' process) than in an expansion culture process using an X-VIVO 10 medium (C process). In the A' process, an expansion culturing rate was higher under the condition of using AIC. Also, the rate of a NK cell after culture and the NKG2D expression rate were equivalent between the A' process and the C process. However, expression of a CD16 molecule which played an important role in exerting antibody-dependent cell-mediated cytotoxicity was higher in the A' process regardless of the presence or the absence of AIC, and it was confirmed that a highly functional NK cell exhibiting high cytotoxic activity was contained in a high proportion.

(8) Measurement of Cytotoxic Activity

Regarding the cells on eighteenth day after culture initiation prepared in Example 29-(5) and Example 29-(6), cytotoxic activity was measured in the same manner as that of Example 1-(5) except provided that A549 was used as a target cell, and measurement was performed at an E/T ratio of 10, 3, 1 and 0.3. Results of measurement of cytotoxic activity are shown in Table 50.

TABLE 50

| | | Cytotoxic activity (%) | | |
|---|---|---|---|---|
| Target cell | E/T ratio | A' process (AIC−) | A' process (AIC+) | C process |
| A549 | 10 | 77.6 | 78.4 | 60.6 |
| | 3 | 75.1 | 77.2 | 54.3 |
| | 1 | 52.8 | 55.3 | 31.2 |
| | 0.3 | 28.3 | 23.9 | 5.6 |

As shown in Table 50, it was made clear that a cell population obtained by the A' process exhibited higher cytotoxic activity on an MHC class I-expressing cell strain A549 than the C process, regardless of the presence or the absence of use of AIC.

That is, it was made clear that, in expansion culture of a NK cell according to the present invention, even when a purified peripheral blood CD3-negative CD56-positive cell was used as a culture initiation cell, a remarkably higher expansion culturing rate was exhibited, and a NK cell having high cytotoxicity could be cultured at a high purity, as compared with other culture processes.

Example 30

Comparison of Activity Between NK Cell and Peripheral Blood-Derived CD3-Negative CD56-Positive Cell after Expansion Culturing (1) Preparation of Anti-Human CD3 Antibody and RetroNectin-Immobilized Plate In the same manner as that of Example 18-(1), an anti-human CD3 antibody and RetroNectin-immobilized plate was prepared.

(2) Expansion Culture of Anti-CD3 Antibody/RetroNectin-Stimulated T Cell

In the same manner as that of Example 3-(2), expansion culture of RN-T was performed.

(3) Preparation of RN-T AIC

In the same manner as that of Example 18-(3), RN-T-AIC was prepared.

(4) Purification of Peripheral Blood CD3-Negative CD56-Positive Cell

In the same manner as that of Example 29-(4), a CD3-negative CD56-positive cell was purified.

(5) Expansion Culture of NK Cell Population Using OK-432 and AIC

Expansion culture of a NK cell population was performed using PBMC or a purified CD3-negative CD56-positive cell. Expansion culturing using PBMC was performed in the same manner as that of Example 28-(4). Expansion culturing using a purified CD3-negative CD56-positive cell was performed in the same manner as that of Example 29-(5) except that only the AIC addition condition was performed.

(6) Measurement of Cell Number after Expansion Culture

In expansion culture of a NK cell population in Example 30-(5), on eighteenth day after culture initiation, the number of live cells was measured by a trypan blue staining method, and the number was compared with the cell number at culture initiation to calculate an expansion culturing rate. Results are shown in Table 51.

TABLE 51

| Culture initiation cell condition | Expansion culturing rate |
| --- | --- |
| PBMC | ×124.4 |
| CD3+CD56− | ×127.0 |

As shown in Table 51, it was made clear that, in expansion culture of a NK cell population using OK-432 and AIC, an equivalent expansion culturing rate was obtained when a culture initiation cell was either PBMC or a purified CD3-negative CD56-positive cell.

(7) Analysis of Surface Antigen

In the same manner as that of Example 14-(4), a T cell content rate, a NK cell content rate and a CD16-positive CD56-positive cell content rate were analyzed, using the purified peripheral blood CD3-negative CD56-positive cell of Example 30-(4) and the cell after culture of Example 30-(5). Results are shown in Table 52.

TABLE 52

| | | Cell content rate (%) | | |
| --- | --- | --- | --- | --- |
| | | CD3+ CD56− | CD3− CD56+ | CD16+ CD56+ |
| Before culture | Purified peripheral blood CD3−CD56+ | 5.4 | 92.6 | 87.4 |
| 18th day after culture initiation | Cultureinitiation cell condition | | | |
| | PBMC | 0.8 | 99.7 | 96.5 |
| | CD3−CD56+ | 0.0 | 99.6 | 96.6 |

As shown in Table 52, it was made clear that, in expansion culture of a NK cell population using OK-432 and AIC, in either case where PBMC or a purified CD3-negative CD56-positive cell is used as a culture initiation cell, a highly functional NK cell equally exhibiting a high purity and a high CD16-positive rate was obtained. In addition, a cell on eighteenth day after culture initiation had a higher CD16 expression rate as compared with a CD3-negative CD56-positive cell before culture, and it was shown that a cell population expansion-cultured by the present invention was a functionally excellent cell population.

(8) Measurement of Cytotoxic Activity

In the same manner as that of Example 14-(5), cytotoxic activity was measured, using the purified peripheral blood CD3-negative CD56-positive cell of Example 30-(4) and the cell after culture of Example 30-(5). Results are shown in Table 53.

TABLE 53

| | | Cytotoxic activity (%) | | |
| --- | --- | --- | --- | --- |
| | | Before culture Purified peripheral blood CD3− | 18th day after culture initiation Culture initiation cell condition | |
| Target cell | E/T ratio | CD56+ | PBMC | CD3−CD56+ |
| K562 | 10 | 89.9 | 78.9 | 93.2 |
| | 3 | 61.0 | 79.8 | 91.3 |
| | 1 | 27.1 | 46.9 | 71.4 |
| | 0.3 | 8.1 | 21.0 | 46.1 |
| A549 | 10 | 11.0 | 68.8 | 78.4 |
| | 3 | 10.1 | 54.5 | 77.2 |
| | 1 | 6.1 | 28.0 | 55.3 |
| | 0.3 | 4.4 | 14.3 | 23.9 |

As shown in Table 53, it was made clear that cell populations obtained by expansion culture of a NK cell population using OK-432 and AIC exhibited higher cytotoxic activity on various target cells than that of a purified peripheral blood CD3-negative CD56-positive cell, in either case where PBMS or a purified CD3-negative CD56-positive cell was used as a culture initiation cell. The difference in the activity was remarkably confirmed for an MHC class I-expressing cell strain A549, and it was confirmed that these cell populations were highly functional NK cells exerting cytotoxic activity on a variety of cancer cell strains. Further, it was made clear that a NK cell population exhibiting further higher cytotoxic activity was obtained by using a purified CD3-negative CD56-positive cell as a culture initiation cell.

That is, it was made clear that the present invention was a culture process having the effect of enhancing functionality of a peripheral blood CD3-negative CD56-positive cell.

Example 31

Comparison Between NK Cell Culture Using OK-432 and AIC and Various NK Cell Culture Process (1) Preparation of Anti-Human CD3 Antibody and RetroNectin-Immobilized Plate In the same manner as that of Example 18-(1), an anti-human CD3 antibody and RetroNectin-immobilized plate was prepared.

(2) Expansion Culture of Anti-CD3 Antibody/RetroNectin-Stimulated T Cell

Expansion culture of RN-T was performed in the same manner as that of Example 12-(2) except that the culture period was for 15 days.

(3) Preparation of AIC Using RN-T

Using the RN-T prepared in Example 31-(2), AIC was prepared in the same manner as that of Example 5-(3) except that the RN-T AIC prepared using the RN-T on eighth day after culture initiation was suspended in 0.8HCellGro at $2 \times 10^6$ cells/mL, and the RN-T AIC prepared using the RN-T on fifteenth day after culture initiation was suspended in 0.8HCellGro at $1 \times 10^6$ cells/mL.

(4) Expansion Culture of NK Cell Population Using OK-432 and AIC

Expansion culture of a NK cell was performed in the same manner as that of Example 17-(1) except that on seventh day after culture initiation, 1.4 mL of a cell liquid of each well was transferred to a new T25 cell culture flask, and 6-fold diluted using 0.8HCellGro. The same subculturing operation was performed on eleventh day and fourteenth day, and culture was continued until sixteenth day. The dilutions of the cell liquids on eleventh day and fourteenth day after culture initiation were 5-hold dilution with 0.8HGT-T502, and 3-fold dilution with 0.3HGT-T502, respectively. On seventh day after culture initiation, each $2.5 \times 10^6$ cells/flask of two kinds of the RN-T AICs prepared in Example 31-(3) were added. Culture was continued until sixteenth day after culture initiation. In the present Example and Example 32, hereinafter, the present process is referred to as A" process.

(5) Preparation of Anti-Human CD16 Antibody-Immobilized Flask

Each 0.57 mL/flask of DPBS containing LEAF purified anti-human CD16 (manufactured by BioLegend, Inc.; hereinafter, referred to as anti-human CD16 antibody) having a final concentration of 1 μg/mL was added to a T25 cell culture flask, and the necessary number of flasks were prepared, and incubated at 37° C. overnight in the presence of 5% $CO_2$. The anti-human CD16 antibody-immobilized flask was washed two times with DPBS immediately before use.

(6) Expansion Culture of NK Cell Population Using OK-432 and Anti-Human CD16 Antibody (Reference Publication: JP-A 2007-297291, JP-B 4275680)

PBMC prepared in the same manner as that of Example 1-(1) was suspended with an AIM V Medium (manufactured by Invitrogen Corporation, hereinafter, referred to as 5HAIM V) containing 5% human type AB serum, at $1 \times 10^6$ cells/mL, and each 1.7 mL/flask of the suspension was added to the anti-human CD16 antibody-immobilized flask prepared in Example 31-(5). OK-432 was added to each flask in a final concentration of 0.01 KE/mL, and IL-2 was added to each flask in a final concentration of 700 U/mL and, in these flasks, culture was initiated at 39° C. in the presence of 5% $CO_2$ (culture $0^{th}$ day), provided that on first day and thereafter, these flasks were cultured at 37° C. in the presence of 5% $CO_2$. On fourth day, the all amount of a cell liquid of each flask was recovered, and centrifuged 320×g and room temperature and, thereafter, the supernatant was removed. After cells recovered from each flask were suspended with 5HAIM V to $1 \times 10^6$ cells/mL, the all amount was added to a new T25 cell culture flask. On sixth day, a cell liquid of each flask was diluted using 5HAIM V at $0.1 \times 10^6$ cells/mL, so that the total was 1.3 mL/flask, and the dilution was added to a new T25 cell culture flask. On eleventh day, 2.6 mL of 5HAIM V was added to each flask, so that the total was 3.9 mL/flask. In addition to the fourth day after culture initiation, sixth day and eleventh day, on fourteenth day, IL-2 was added to each flask in a final concentration of 700 U/mL, and culture was continued until sixteenth day. In the present Example, hereinafter, the present process is referred to as D process.

(7) Preparation of Anti-Human CD52 Antibody and Anti-Human CD3 Antibody-Immobilized Plate Each 0.5 mL/well of DPBS containing an anti-human CD3 antibody having a final concentration of 0.1 μg/mL and RAT ANTI HUMAN CD52 (manufactured by AbD Serotec; hereinafter, referred to as anti-human CD52 antibody) having a final concentration of 20 μg/mL was added to a 24-well cell culture plate to make the necessary number of wells, and the plate was allowed to stand at 4° C. overnight. The anti-human CD52 antibody/anti-human CD3 antibody-immobilized plate was washed two times with DPBS immediately before use.

(8) Expansion Culture of NK Cell Population Using Anti-Human CD3 Antibody and Anti-Human CD52 Antibody (Reference Publication: JP-A 2006-340698)

After PBMC prepared in the same manner as that of Example 1-(1) was suspended with KBM540 (manufactured by KOHJIN BIO Co., Ltd.) at $1 \times 10^6$ cells/mL, each 1 mL/well of the suspension was added to the anti-human CD52 antibody/anti-human CD3 antibody-immobilized plate prepared in Example 31-(7). On third day, each 1 mL of KBM540 was added to each flask, so that the total was 2 mL/flask. On fifth day, 1 mL of a cell liquid of each flask was transferred to a new 6-well cell culture plate (manufactured by Becton, Dickinson and Company, or manufactured by Corning Incorporated), and 11-fold diluted using KBM540. The same subculturing operation was performed on ninth day and fourteenth day, and the dilution of each cell liquid was 2-fold dilution with KBM540. In addition to the third day, fifth day, ninth day and fourteenth day after culture initiation, on seventh day and eleventh day, IL-2 was added to each well in a final concentration of 200 U/mL, and culturing was continued until sixteenth day. In the present Example, hereinafter, the present process is referred to as E process.

(9) Cell Number Measurement

In expansion culture of a NK cell population of Example 31-(4), Example 31-(6) and Example 31-(8), on sixteenth day after culture initiation, the number of live cells was measured by a trypan blue staining method, and the number was compared with the cell number at culture initiation to calculate an expansion culturing rate. Results are shown in Table 54.

TABLE 54

| Culture process | Expansion culturing rate $16^{th}$ day after NK Culture initiation |
|---|---|
| A" process | ×158.6 |
| D process | ×33.3 |
| E process | ×174.9 |

(10) Analysis of Surface Antigen of Cell Population after Culture

Regarding the cells on sixteenth day after culture initiation prepared in Example 31-(4), Example 31-(6) and Example 31-(8), CD3-positive CD56-negative cell (T cell), CD3-negative CD56-positive cell (NK cell) and CD16-positive CD56-positive cell content rates, and a CD56-positive NKG2D-positive cell content rate were analyzed in the same manner as that of Example 14-(4) except that a CD69-positive CD56 positive cell content rate and a CXCR3-positive CD56-positive cell content rate were also analyzed using a FITC-labeled mouse anti-human CD69 antibody (manufactured by eBioscience, Inc.), and a FITC labeled mouse anti-human CXCR3 antibody (manufactured by R&D Systems, Inc.). Results are shown in Table 55.

TABLE 55

| Culture process | Cell content rate (%) | | | | | |
|---|---|---|---|---|---|---|
| | CD3+ CD56− | CD3− CD56+ | CD16+ CD56+ | NKG2D+ CD56+ | CD69+ CD56+ | CXCR3+ CD56+ |
| A" process | 0.2 | 99.4 | 99.2 | 97.8 | 34.2 | 63.3 |
| D process | 46.7 | 36.2 | 53.2 | 56.8 | 7.1 | 29.2 |
| E process | 82.2 | 3.5 | 6.2 | 20.3 | 4.8 | 17.5 |

As shown in Table 54, in an expansion culture process using OK432 and AIC (A" method), an expansion culturing rate was equivalent to that of an expansion culture process using an anti-human CD3 antibody and an anti-human CD52 antibody (E process), and was higher as compared with an expansion culture process using OK432 and an anti-human CD16 antibody (D process). As shown in Table 55, the rate of a NK cell after culture was remarkably high in the A" process, and the NK cell expressed CD16, NKG2D, CD69 and CXCR3 at further higher rates. CD69, also known as activation inducer molecule (AIM), is expressed at an initial stage of activation of a leukocyte, and is involved in target cytolysis action of a NK cell. CXCR3 is a ligand for CXCL9 and CXCL10 which are a chemokine, and is thought to exhibit the high ability to migrate to these chemokine-expressing cancer cells and the high ability to accumulate into those cells. Therefore, it was confirmed that the NK cell obtained by the A" process contained a high proportion of a highly functional NK cell expressing CD16, NKG2D, CD69 and CXCR3 at a high rate and, at the same time, contained a high proportion of a NK cell thought to have the high ability to migrate to a cancer cell and the high ability to accumulate locally in a living body, and it was made clear that the NK cell was a NK cell population which was expected to exert extremely excellent anti-tumor activity.

(11) Measurement of Cytotoxic Activity

Regarding the cells on sixteenth day after culture initiation prepared in Example 31-(4), Example 31-(6) and Example 31-(8), cytotoxic activity was measured in the same manner as that of Example 14-(5). Results of measurement of cytotoxic activity are shown in Table 56.

TABLE 56

| Target cell | E/T ratio | Cytotoxic activity (%) | | |
|---|---|---|---|---|
| | | A" | D process | E process |
| K562 | 1 | 69.2 | 66.1 | 5.2 |
| | 0.3 | 41.8 | 32.4 | 1.9 |

TABLE 56-continued

| Target cell | E/T ratio | Cytotoxic activity (%) | | |
|---|---|---|---|---|
| | | A" | D process | E process |
| A549 | 10 | 80.4 | 39.5 | −2.9 |
| | 3 | 76.4 | 14.1 | −6.4 |
| | 1 | 55.1 | −0.7 | −9.1 |
| | 0.3 | 22.0 | −6.4 | −10.9 |

As shown in Table 56, it was made clear that the cell population obtained by the A" process exhibited high cytotoxic activity on various target cells. The activity was confirmed on not only K562 known as a NK cell-sensitive cell strain, but also an MHC class I-expressing cell strain A549, and it was confirmed that this cell population was a highly functional NK cell exerting cytotoxic activity on a variety of cancer cell lines.

That is, it was made clear that the A" process of the present invention was a culture process by which a cell population exhibiting a CD3-negative CD56-positive CD16-positive phenotype, and having higher cytotoxicity could be obtained at a good purity as compared with known NK cell culture processes such as the D process and the E process.

Example 32

Comparison Between NK Cell Culture Using OK-432 and AIC and Various NK Cell Culture Processes (Comparison of Initial Stimulation Under the Condition of the Same Basal Culture Medium)

(1) Preparation of Anti-Human CD3 Antibody and RetroNectin-Immobilized Plate

In the same manner as that of Example 18-(1), an anti-human CD3 antibody RetroNectin-immobilized plate was prepared.

(2) Expansion Culture of Anti-CD3 Antibody/RetroNectin-Stimulated T Cell

In the same manner as that of Example 31-(2), expansion culture of RN-T was performed.

(3) Preparation of AIC Using RN-T

In the same manner as that of Example 31-(3), AIC was prepared.

(4) Expansion Culture of NK Cell Population (NK Cell Culture Using OK-432 and AIC)

In the same manner as that of Example 31-(4), expansion culture of a NK cell was performed (A" method).

(5) Preparation of Anti-Human CD16 Antibody-Immobilized Plate

Each 0.217 mL/well of DPBS containing an anti-human CD16 antibody having a final concentration of 1 μg/mL was added to a 12-well cell culture plate to make the necessary number of wells, and the plate was incubated at 37° C. overnight in the presence of 5% CO$_2$. The anti-human CD16 antibody-immobilized plate was washed two times with DPBS immediately before use.

(6) Expansion Culture of NK Cell Population Using OK-432 and Anti-Human CD16 Antibody (Reference Publication: JP-A 2007-297291, JP-B 4275680)

After PBMC prepared in the same manner as that of Example 1-(1) was suspended with 0.8HCellGro at 1×10$^6$ cells/mL, each 1.9 mL/well of the suspension was added to the anti-human CD16 antibody-immobilized plate prepared in Example 32-(5). OK-432 was added to each well in a final concentration of 0.05 KE/mL, IL-2 was added to each well in a final concentration of 200 U/mL, and culture was initiated at 39° C. in the presence of 5% $CO_2$ (culture 0th day), provided that on first day and thereafter, culture was performed at 37° C. in the presence of 5% $CO_2$. On second day, each 1.9 mL of 0.8HCellGro was added to each well, so that the total was 3.8 mL/well. On fourth day, the all amount of a cell liquid of each well was recovered, and centrifuged at 320×g and room temperature and, thereafter, the supernatant was removed. After cells recovered from each well were suspended with 3.8 mL of 0.8HCellGro, the all amount was added to a new 12-well cell culture plate. On seventh day, 1.4 mL of a cell liquid of each flask was 6-fold diluted with 0.8 HCellGro, and added to a new T25 cell culture flask. In addition to the second day, fourth day and seventh day after culture initiation, on eleventh day and fourteenth day, IL-2 was added to each flask in a final concentration of 200 U/mL, and culture was continued until sixteenth day. In the present Example, hereinafter, the present process is referred to as D' process.

(7) Preparation of Anti-Human CD52 Antibody and Anti-Human CD3 Antibody-Immobilized Plate Each 0.95 mL/well of DPBS containing an anti-human CD3 antibody having a final concentration of 0.1 μg/mL and an anti-human CD52 antibody having a final concentration of 20 μg/mL was added to a 24-well cell culture plate to make the necessary number of wells, and this was allowed to stand at 4° C. overnight. The anti-human CD52 antibody/anti-human CD3 antibody-immobilized plate was two times washed with DPBS immediately before use.

(8) Expansion Culture of NK Cell Population using Anti-Human CD3 Antibody and Anti-Human CD52 Antibody (Reference Publication: JP-A 2006-340698)

After PBMC prepared in the same manner as that of Example 1-(1) was suspended with 0.8HCellGro at $1\times10^6$ cells/mL, each 1.9 mL/well of the suspension was added to the anti-human CD52 antibody/anti-human CD3 antibody-immobilized plate prepared in Example 32-(7). On third day, each 1.9 mL of 0.8HCellGro was added to each well, so that the total was 3.8 mL/well. On fifth day, 1.4 mL of a cell liquid of each flask was 6-fold diluted with 0.8HCellGro, and added to a new T25 cell culture flask. The same subculturing operation was performed on ninth day, eleventh day and fourteenth day, and culture was continued until sixteenth day. The dilutions of cell liquids of ninth day, eleventh day, and fourteenth day after culture initiation were 2-fold dilution with 0.8HCellGro, 5-fold dilution with 0.8HGT-T502, and 3-fold dilution with 0.3HGT-T502, respectively. In addition to the third day, fifth day, ninth day, eleventh day and fourteenth day after culture initiation, on seventh day, IL-2 was added to each flask in a final concentration of 200 U/mL, and culture was continued until sixteenth day. In the present Example, hereinafter, the present process is referred to as E' process.

(9) Analysis of Surface Antigen of Cell Population after Culture

Regarding the cells on sixteenth day after culture initiation prepared in Example 32-(4), Example 32-(6) and Example 32-(8), CD3-positive CD56-negative cell (T cell), CD3-negative CD56-positive cell (NK cell), a CD16-positive CD56-positive cell content rates, a CD56-positive NKG2D-positive cell content rate, a CD69-positive CD56-positive cell content rate and a CXCR3-positive CD56 positive cell content rate were analyzed in the same manner as that of Example 31-(10). Results are shown in Table 57.

TABLE 57

| Culture process | Cell content rate (%) | | | | | |
|---|---|---|---|---|---|---|
| | $CD3^+$ $CD56^-$ | $CD3^-$ $CD56^+$ | $CD16^+$ $CD56^+$ | $NKG2D^+$ $CD56^+$ | $CD69^+$ $CD56^+$ | $CXCR3^+$ $CD56^+$ |
| A" process | 0.2 | 99.4 | 99.2 | 97.8 | 34.2 | 63.3 |
| D' process | 15.0 | 80.7 | 69.7 | 67.9 | 0.4 | 1.9 |
| E' process | 71.4 | 12.6 | 14.9 | 32.0 | 6.3 | 22.1 |

As shown in Table 57, the rate of a NK cell after culture was remarkably high in the A" process, and the NK cell expressed CD16, NKG2D, CD69 and CXCR3 at further higher rates. It was confirmed that the NK cell obtained by the A" process contained a high proportion of a highly functional NK cell expressing CD16, NKG2D, CD69 and CXCR3 at a high rate and, at the same time, contained a high proportion of a NK cell thought to have the high ability to migrate to a cancer cell and the high ability to accumulate locally in a living body, and it was made clear that the NK cell was a NK cell population which was expected to exert extremely excellent anti-tumor activity.

(10) Measurement of Cytotoxic Activity

Regarding the cells of sixteenth day after culture initiation prepared in Example 32-(4), Example 32-(6) and Example 32-(8), cytotoxic activity was measured in the same manner as that of Example 14-(5) except that the measurement was performed at an E/T ratio of 3, 1 and 0.3. Results of measurement of cytotoxic activity are shown in Table 58.

TABLE 58

| Target cell | E/T ratio | Cytotoxic activity (%) | | |
|---|---|---|---|---|
| | | A" process | D' process | E' process |
| K562 | 3 | 72.9 | 58.1 | 41.6 |
| | 1 | 69.2 | 30.7 | 12.7 |
| | 0.3 | 41.8 | 10.6 | 2.5 |
| A549 | 3 | 76.4 | 7.7 | 8.4 |
| | 1 | 55.2 | −0.7 | −4.9 |
| | 0.3 | 22.0 | −5.1 | −9.0 |

As shown in Table 58, it was made clear that the cell population obtained by the A" process exhibited high cytotoxic activity on various target cells. The activity was confirmed on not only K562 known as a NK cell-sensitive cell strain, but also an MHC class I-expressing cell strain A549, and it was confirmed that this cell population was a highly functional NK cell exerting cytotoxic activity on variety of cancer cell lines.

That is, it was made clear that the A" process which was the present invention is a culture process by which a cell population exhibiting a CD3-negative CD56-positive CD16-positive phenotype and having higher cytotoxicity could be obtained at a good purity, as compared with known NK cell culture processes such as the D' process and the E' process. Hence, the culture process of the present invention (NK cell stimulating process) is extremely more excellent than known NK cell culture processes (NK cell stimulating processes), even under the same condition of a culture medium. It was suggested that immunotherapy, high therapeutic effect of which could be expected, could be provided by the present invention.

Industrial Applicability

According to the present invention, a process of expansion-culturing a NK cell is provided. The process has a high cell proliferation rate, and the cell population containing a NK cell obtained by the present invention is excellent in cytotoxic activity, and is extremely useful in the medical field including adoptive immunotherapy.

The invention claimed is:

1. A process for preparing a cell population containing a natural killer cell, comprising,
    providing a first cell population containing a T cell that has been expansion-cultured in the presence of an anti-CD3 antibody, or an anti-CD3 antibody and a polypeptide having an amino acid sequence derived from fibronection, and then subjected to a treatment which diminishes its proliferation ability,
    expansion-culturing a second cell population containing a natural killer cell and/or a cell capable of differentiating into a natural killer cell, in the presence of the first cell population and a preparation derived from *Streptococcus pyogenes* or *Bacillus Calmette Guerin* (BCG) or a preparation derived from BCG cell wall.

2. The process according to claim 1, wherein the preparation is a preparation derived from *Streptococcus pyogenes* and is OK-432.

3. The process according to claim 1, wherein the T cell was derived from the same individual as that of the natural killer cell or the cell capable of differentiating into a natural killer cell.

4. The process according to claim 1, wherein the expansion-culturing comprises adding the first cell population a plural number of times.

5. The process according to claim 1, wherein a peripheral blood mononuclear cell is used as the natural killer cell and/or the cell capable of differentiating into a natural killer cell.

6. A process for preparing a cell population containing a natural killer cell, comprising the steps of:

(i) expansion-culturing a cell population containing a T cell or a precursor T cell in the presence of an anti-CD3 antibody, or an anti-CD3 antibody and a polypeptide having an amino acid sequence derived from fibronection to prepare an expansion-cultured T cell population, and diminishing proliferation ability of the expansion-cultured T cell population, and (ii) expansion-culturing a cell population containing a natural killer cell and/or a cell capable of differentiating into a natural killer cell, in the presence of a preparation derived from *Streptcoccus pyogenes* or *Bacillus Calmette Guerin* (BCG) or a preparation derived from BCG cell wall, and the expansion-cultured T cell population of which the proliferation ability has been diminished obtained by step (i).

7. A process for preparing a cell population containing a natural killer cell, comprising a step of expansion-culturing a cell population containing a natural killer cell and/or a cell capable of differentiating into a natural killer cell, in the presence of a bioresponse modifying agent and a T-cell which has been subjected to a treatment which diminishes its proliferation ability,
    wherein the bioresponse modifying agent is a bacterium-derived preparation, and wherein the T-cell which has been subjected to a treatment which diminishes its proliferation ability is an expansion-cultured T-cell population which has been subjected to a treatment which diminishes it proliferation ability, and
    wherein the proportion of natural killer cells after 21 days of expansion culturing is increased by at least 333-fold.

* * * * *